United States Patent
Ghosh et al.

(10) Patent No.: US 10,918,863 B2
(45) Date of Patent: Feb. 16, 2021

(54) GENERATING ACTIVATION TIMES

(71) Applicant: Medtronic, Inc., Minneapolis, MN (US)

(72) Inventors: Subham Ghosh, Blaine, MN (US); Karen J. Kleckner, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 235 days.

(21) Appl. No.: 16/047,625

(22) Filed: Jul. 27, 2018

(65) Prior Publication Data

US 2019/0030332 A1 Jan. 31, 2019

Related U.S. Application Data

(60) Provisional application No. 62/538,396, filed on Jul. 28, 2017.

(51) Int. Cl.
| | |
|---|---|
| *A61B 5/0452* | (2006.01) |
| *A61N 1/36* | (2006.01) |
| *A61B 5/0408* | (2006.01) |
| *A61B 5/0531* | (2021.01) |
| *A61N 1/04* | (2006.01) |
| *A61N 1/362* | (2006.01) |

(Continued)

(52) U.S. Cl.
CPC .......... *A61N 1/3603* (2017.08); *A61B 5/0452* (2013.01); *A61B 5/04085* (2013.01); *A61B 5/0531* (2013.01); *A61N 1/0484* (2013.01); *A61N 1/3625* (2013.01); *A61B 5/024* (2013.01); *A61B 5/02405* (2013.01); *A61B 5/0456* (2013.01); *A61B 5/0464* (2013.01); *A61B 5/0468* (2013.01); *A61B 5/0472* (2013.01); *A61B 5/4836* (2013.01); *A61B 5/6823* (2013.01); *A61B 5/6831* (2013.01); *A61B 2562/046* (2013.01); *A61N 1/362* (2013.01)

(58) Field of Classification Search
CPC . A61B 5/04085; A61B 5/0452; A61B 5/0456; A61B 5/0468; A61B 5/0472
See application file for complete search history.

(56) References Cited

U.S. PATENT DOCUMENTS

| | | |
|---|---|---|
| 4,233,987 A | 11/1980 | Feingold |
| 4,402,323 A | 9/1983 | White |

(Continued)

FOREIGN PATENT DOCUMENTS

| | | |
|---|---|---|
| CN | 1043621 A | 7/1990 |
| CN | 1253761 A | 5/2000 |

(Continued)

OTHER PUBLICATIONS

International Search Report and Written Opinion dated Nov. 7, 2018 for International Application No. PCT/US2018/043923; 15 pages.

(Continued)

*Primary Examiner* — Allen Porter
(74) *Attorney, Agent, or Firm* — Mueting Raasch Group

(57) ABSTRACT

Systems and methods are described herein for generating surrogate cardiac electrical activation times from electrical activity monitored by a plurality of external electrodes. Surrogate cardiac electrical activation times that should be corrected may be identified, or determined, according to one or more metrics, and then such surrogate cardiac electrical activation times may be corrected according to various criterion.

58 Claims, 15 Drawing Sheets

(51) Int. Cl.
*A61B 5/00* (2006.01)
*A61B 5/0468* (2006.01)
*A61B 5/024* (2006.01)
*A61B 5/0472* (2006.01)
*A61B 5/0464* (2006.01)
*A61B 5/0456* (2006.01)

(56) References Cited

U.S. PATENT DOCUMENTS

| | | |
|---|---|---|
| 4,428,378 A | 1/1984 | Anderson et al. |
| 4,497,326 A | 2/1985 | Curry |
| 4,566,456 A | 1/1986 | Koning et al. |
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,238,158 B2 | 7/2007 | Abend |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harley et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |

(56) References Cited

U.S. PATENT DOCUMENTS

| | | |
|---|---|---|
| 8,731,642 B2 | 5/2014 | Zarkh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,861,830 B2 | 10/2014 | Brada et al. |
| 8,972,228 B2 | 3/2015 | Ghosh et al. |
| 9,037,238 B2 | 5/2015 | Stadler et al. |
| 9,132,274 B2 | 9/2015 | Ghosh et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 9,474,457 B2 | 10/2016 | Ghosh et al. |
| 9,486,151 B2 | 11/2016 | Ghosh et al. |
| 9,510,763 B2 | 12/2016 | Gosh et al. |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,764,143 B2 | 9/2017 | Ghosh et al. |
| 9,776,009 B2 | 10/2017 | Ghosh et al. |
| 9,789,319 B2 | 10/2017 | Sambelashvili |
| 9,924,884 B2 | 3/2018 | Ghosh et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0167809 A1 | 7/2007 | Dala-Krishna |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |

(56) References Cited

U.S. PATENT DOCUMENTS

| | | |
|---|---|---|
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0190834 A1 | 7/2013 | Ghosh et al. |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0184590 A1 | 6/2016 | Ghosh |
| 2016/0331258 A1 | 11/2016 | Du et al. |
| 2017/0246460 A1 | 8/2017 | Ghosh |
| 2017/0246461 A1 | 8/2017 | Ghosh |
| 2017/0143976 A1 | 11/2017 | Tazawa et al. |
| 2018/0263522 A1 | 9/2018 | Ghosh et al. |
| 2018/0264258 A1 | 9/2018 | Cheng et al. |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

International Search Report and Written Opinion dated May 3, 2012 for International Application No. PCT/US2012/036262; 9 pages.
International Search Report and Written Opinion dated May 3, 2012 for International Application No. PCT/US2012/036302; 9 pages.
International Search Report and Written Opinion dated Aug. 6, 2014 for International Application No. PCT/US2014/036153; 14 pages.
International Search Report and Written Opinion dated Nov. 7, 2014 for International Application No. PCT/US2014/036163; 12 pages.
International Search Report and Written Opinion dated Oct. 28, 2014 for International Application No. PCT/US2014/041928; 15 pages.
International Search Report and Written Opinion dated Oct. 24, 2014 for International Application No. PCT/US2014/041929; 14 pages.
International Search Report and Written Opinion dated Nov. 4, 2014 for International Application No. PCT/US2014/0247583; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
International Search Report and Written Opinion dated Mar. 9, 2015 for International Application No. PCT/US2014/069214; 11 pages.
International Search Report and Written Opinion dated Mar. 17, 2015, for International Application No. PCT/US2014/069192; 11 pages.
International Search Report and Written Opinion dated Mar. 16, 2015 for International Application No. PCT/US2014/069182; 11 pages.
International Search Report and Written Opinion dated Apr. 8, 2015 for International Application No. PCT/US2014/069070; 11 pages.

(56) References Cited

OTHER PUBLICATIONS

International Search Report and Written Opinion dated Jun. 11, 2015 for International Application No. PCT/US2015/021442; 13 pages.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
Botker MD, PhD., et al., "Electromechanical Mapping for Detection of Myocardial Viability in Patients with ischemia Cardiomyopathy," Circulation, Mar. 2001; vol. 103, No. 12, pp.
"CardioGuide System Enables Real-Time Navigation of Left Ventricular Leads During Medtronic CRT Implants," Press Release, Apr. 9, 2013, Medtronic, Inc., 2 pgs.
Cuculich, P.S., et al., "The Electrophysiological Cardiac Ventricular Substrate in Patients After Myocardial Infection" J. Am. Coll. Cardiol. 2011; 58:1893-1902.
Czerwinska et al., "Method of Segmentation of Thorax Organs Images Applied to Modeling the Cardiac Electrical Field," *Engineering in Medicine and Biology Society*, Proceedings of the $22^{nd}$ Annual International Conference of the IEEE, vol. 1, 23, Jul. 23, 2000.; pp. 402-405.
Dawoud, F. et al., "Inverse Electrocardiographic Imaging to Assess Electrical Dyssynchrony in Cardiac Resynchronization Therapy Patients," Computing in Cardiology, 2012; 39:993-996.
Freund et al., "A Decision-Theoretic Generalization of Online Learning and an Application to Boosting," *Journal of Computer and System Sciences*, 1997; 55(1):119-139.
Friedman, "Greedy Function Approximation: A Gradient Boosting Machine," *Annals of Statistics*, 2001; 29(5):1189-1232.
Friedman, "Stochastic Gradient Boosting," *Computational Statistics and Data Analysis*, 2002; 38(4):367-378.
Friedman et al., "Additive Logistic Regression: a Statistical View of Boosting," *Annals of Statistics*, 2000; 28(2):337-374.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar., 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," *Heart Rhythm*, Sep. 2011; 8(9): 1469-1475.
"Heart Failure Management" datasheet [online]. Medtronic, Minneapolis, Minnesota, [Last updated on Jun. 3, 2013].Retrieved from the Internet: www.medtronic.com; 9 pages.
Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Lumason™, Brochure, Bracco Diagnostocs. Oct. 2014.
Medtronic Vitatron Carelink Encore® Programmer Model 29901 Reference Manual, 2013, Medtronic, Inc., Minneapolis, MN.
Miri et al., "Applicability of body surface potential map in computerized optimization of biventricular pacing," Annals of Biomedical Engineering, vol. 38, No. 3, Mar. 2010, pp. 865-875.
Miri et al., "Comparison of the electrophysiologically based optimization methods with different pacing parameters in patient undergoing resynchronization treatment," 30th Annual International IEEE EMBS Conference, Aug. 2008, pp. 1741-1744.
Miri et al., "Computerized Optimization of Biventricular Pacing Using Body Surface Potential Map," 31st Annual International Conference of the IEEE EMBS, Sep. 2009, pp. 2815-2818.
Miri et al., "Efficiency of Timing Delays and Electrode Positions in Optimization of Biventricular Pacing: A Simulation Study," IEEE Transactions on Biomedical Engineering, Nov. 2009, pp. 2573-2582.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Ridgeway, "The State of Boosting," *Computing Science and Statistics*, 1999; 31:172-181.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms: a simulation study," Circulation Research, 1989, 64:449-462.
Strik et al., "Electrical and Mechanical Ventricular Activation During Left Bundle Branch Block and Resynchronization," *J. of Cardiovasc. Trans. Res.*, 2012; 5:117-126.
Svendsen et al., "Computational Models of Cardiac Electrical Activation," Chapter 5, Computational Nov. 2010, pp. 73-88.
Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010;121(5):626-34. Available online Jan. 25, 2010.
Sweeney et al., QRS Fusion Complex Analysis Using Wave Interference to Predict Reverse Remodeling During Cardiac Resynchronization Therapy, heart Rhythm, 2014, 11:806-813.

(56) References Cited

OTHER PUBLICATIONS

Turner et al, "Electrical and Mechanical Components of Dyssynchrony in Heart Failure Patients with Normal QRS Duration and Left Bundle-Branch Block," *Circulation* 2004; 109:2544-2549.

Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.

Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.

Varma et al., "Placebo CRT," *Journal of Cardiovascular Electrophysiology*, vol. 19, Aug. 2008; p. 878.

Wang et al., "Application of the Method of Fundamental Solutions to Potential-based Inverse Electrocardiography," Annals of Biomedical Engineering, Aug. 2006, pp. 1272-1288.

Wellens, MD et al., "The Electrocardiogram 102 Years After Einthoven," Circulation, Feb. 2004; vol. 109, No. 5, pp. 562-564.

Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.

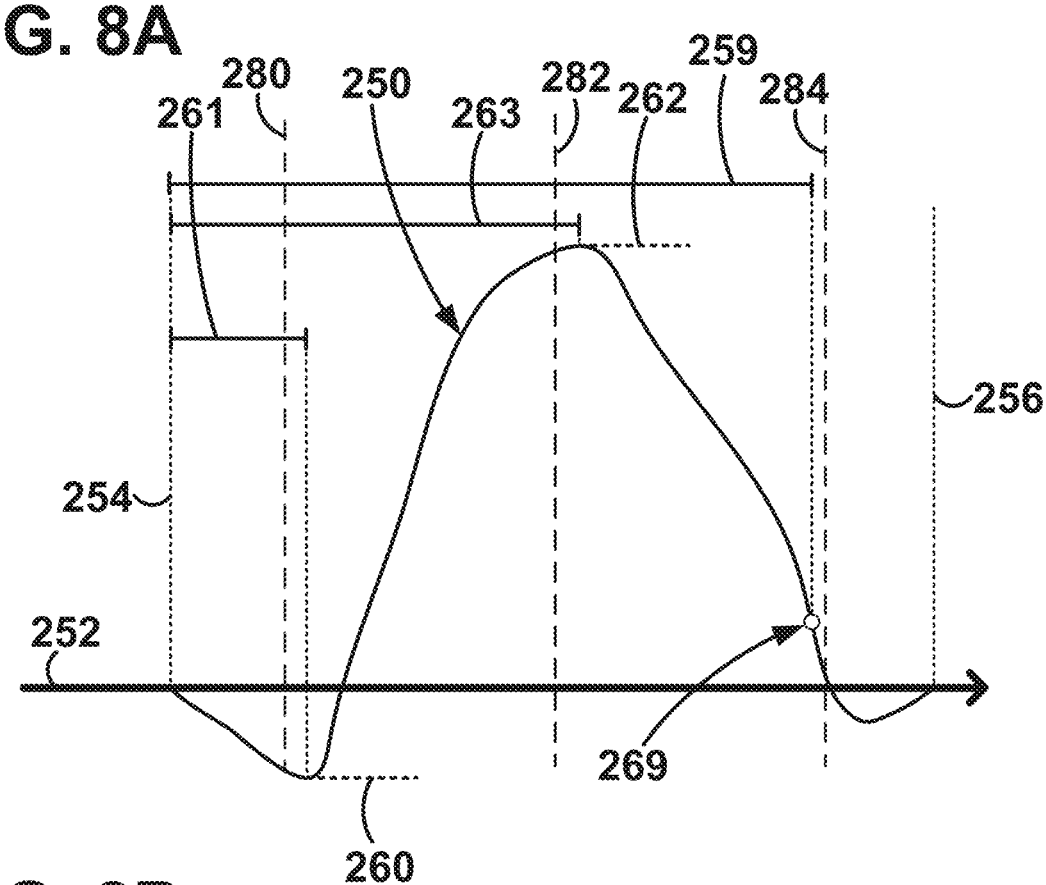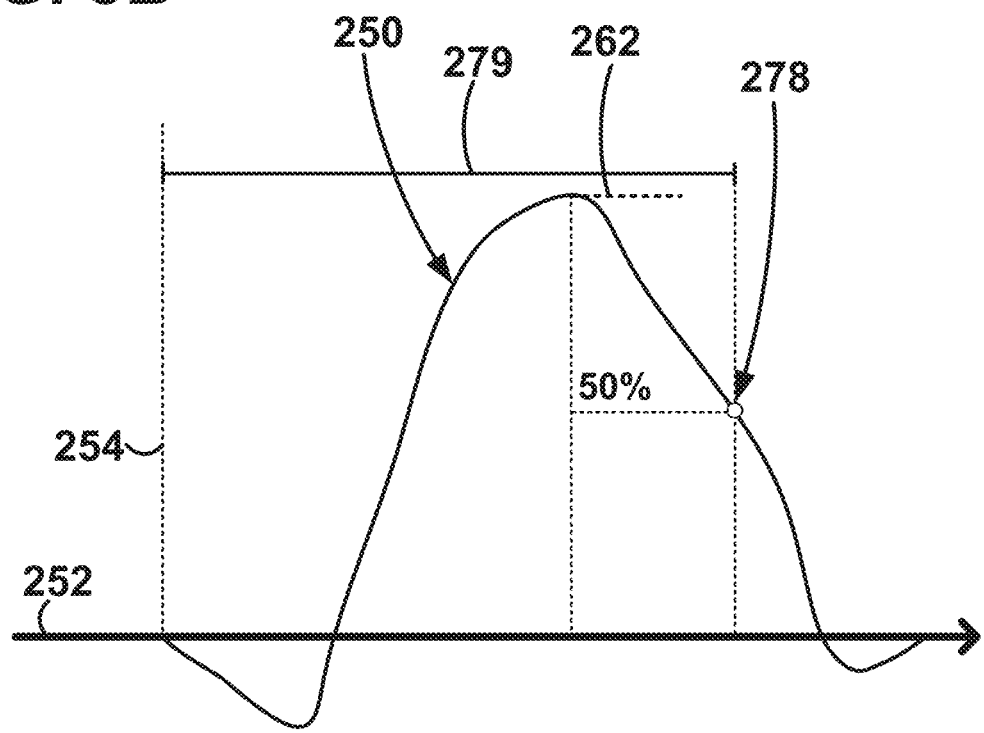

GENERATING ACTIVATION TIMES

This application claims the benefit of U.S. Provisional Patent Application No. 62/538,396, filed Jul. 28, 2017, which is incorporated herein by reference in its entirety.

The disclosure herein relates to systems and methods for use in the generation of cardiac electrical activation times.

Implantable medical devices (IMDs), such as implantable pacemakers, cardioverters, defibrillators, or pacemaker-cardioverter-defibrillators, provide therapeutic electrical stimulation to the heart. IMDs may provide pacing to address bradycardia, or pacing or shocks in order to terminate tachyarrhythmia, such as tachycardia or fibrillation. In some cases, the medical device may sense intrinsic depolarizations of the heart, detect arrhythmia based on the intrinsic depolarizations (or absence thereof), and control delivery of electrical stimulation to the heart if arrhythmia is detected based on the intrinsic depolarizations.

IMDs may also provide cardiac resynchronization therapy (CRT), which is a form of pacing. CRT involves the delivery of pacing to the left ventricle, or both the left and right ventricles. The timing and location of the delivery of pacing pulses to the ventricle(s) may be selected to improve the coordination and efficiency of ventricular contraction.

Systems for implanting medical devices may include workstations or other equipment in addition to the implantable medical device itself. In some cases, these other pieces of equipment assist the physician or other technician with placing the intracardiac leads at particular locations on the heart. In some cases, the equipment provides information to the physician about the electrical activity of the heart and the location of the intracardiac lead. The equipment may perform similar functions as the medical device, including delivering electrical stimulation to the heart and sensing the depolarizations of the heart. In some cases, the equipment may include equipment for obtaining an electrocardiogram (ECG) via electrodes on the surface, or skin, of the patient. More specifically, the patient may have a plurality of electrodes on an ECG belt or vest that surrounds the torso of the patient. After the belt or vest has been secured to the torso, a physician can perform a series of tests to evaluate a patient's cardiac response. The evaluation process can include detection of a baseline rhythm in which no electrical stimuli is delivered to cardiac tissue and another rhythm after electrical stimuli is delivered to the cardiac tissue.

The ECG electrodes placed on the body surface of the patient may be used for various therapeutic purposes (e.g., cardiac resynchronization therapy) including optimizing lead location, pacing parameters, etc. based on one or more metrics derived from the signals captured by the ECG electrodes. For example, electrical heterogeneity information may be derived from electrical activation times computed from multiple electrodes on the body surface.

Further, the signals from multiple electrodes on the body surface can be used to determine one or more specific ECG features such as, e.g., QRS onset, peak, QRS offset, etc. for a series of multiple heartbeats. Such ECG features may be used by themselves to evaluate cardiac health and/or therapy, or may be used to calculate, or compute, activation times. However, in one or more instances, signals upon which activation times are based, or computed from, may contain various anomalies that may, for example, result in less accurate activation times.

SUMMARY

The exemplary systems and methods described herein may be configured to assist users (e.g., physicians) in configuring cardiac therapy (e.g., cardiac therapy being performed on a patient during and/or after implantation of cardiac therapy apparatus). The systems and methods may be described as being noninvasive. For example, the systems and methods may not need implantable devices such as leads, probes, sensors, catheters, etc. to evaluate and configure the cardiac therapy. Instead, the systems and methods may use electrical measurements taken noninvasively using, e.g., a plurality of external electrodes attached to the skin of a patient about the patient's torso.

Further, the exemplary systems and methods may assist users in configuring cardiac therapy by monitoring and using one or more electrical signals taken, or monitored, from the plurality of external electrodes attached to the skin of a patient about the patient's torso. Activation times for at least one (e.g., one, two or more, each of, all, etc.) electrode may be generated or calculated, which may then be used for further analysis of a patient's cardiac health and/or configuration of cardiac therapy (e.g., to be delivered to the patient, being presently delivered to the patient, etc.). The activation times, however, may qualify for correction, or need to be corrected, for various reasons such as, e.g., poor signal, signal artifacts, anomalies, outliers, noise, variations, low-amplitude fusion signals with two descending phases, signals with linear descending phase (slope is nearly constant), etc.

Such activation times may be analyzed and determined to be corrected by the exemplary systems and methods described herein. Then, correction of these such activation times according to various correction criterion may be provided by the exemplary systems and methods described herein.

One exemplary system for use in cardiac evaluation may include electrode apparatus comprising a plurality of external electrodes to be located proximate a patient's skin and computing apparatus (e.g., including one or more processors) coupled to the electrode apparatus and configured to monitor electrical activity from the patient's skin using the plurality of external electrodes over a cardiac cycle, generate a surrogate cardiac electrical activation time based on the monitored electrical activity using baseline criterion, and determine whether to correct the surrogate cardiac electrical activation time. Further, the computing apparatus may be further configured to regenerate the surrogate cardiac electrical activation time based on the monitored electrical activity using correction criterion in response to a determination to correct the surrogate electrical activation time.

One exemplary method for use in cardiac evaluation may include monitoring electrical activity from a patient's skin using a plurality of electrodes to generate over a cardiac cycle and generating a surrogate cardiac electrical activation time based on the monitored electrical activity using baseline criterion. The exemplary method may further include determining whether to correct the surrogate cardiac electrical activation time and regenerating the surrogate cardiac electrical activation time based on the monitored electrical activity using correction criterion in response to a determination to correct the surrogate cardiac electrical activation time.

In one or more embodiments, monitoring electrical activity from the patient's skin using the plurality of external electrodes over a cardiac cycle may include monitoring electrical activity from the patient's skin using the plurality of external electrodes over a cardiac depolarization cycle.

In one or more embodiments, the baseline criterion defines a start time point and an end time point for the surrogate cardiac electrical activation time, and the end time point may correspond to the time at which the maximum negative slope occurs within the electrical activity over the cardiac cycle.

In one or more embodiments, determining whether to correct the surrogate cardiac electrical activation time may include determining to correct the surrogate cardiac electrical activation time with late correction if the surrogate cardiac electrical activation time is greater than or equal to a selected late correction threshold. Further, in one or more embodiments, the selected late correction threshold may be a percentage of a QRS complex time extending from an onset of a QRS complex within the electrical activity over the cardiac cycle to an offset of the QRS complex where the percentage may be greater than or equal to 75%.

In one or more embodiments, determining whether to correct the surrogate cardiac electrical activation time may include determining to correct the surrogate cardiac electrical activation time with early correction if the surrogate cardiac electrical activation time is less than or equal to a selected early correction threshold. Further, in one or more embodiments, the selected early correction threshold may be a percentage of a QRS complex time extending from an onset of a QRS complex within the electrical activity over the cardiac cycle to an offset of the QRS complex where the percentage may be less than or equal to 25%.

In one or more embodiments, determining whether to correct the surrogate cardiac electrical activation time may include determining to correct the surrogate cardiac electrical activation time with late correction if one or more of (e.g., one, some of, all, etc.): right ventricular cardiac pacing or no cardiac pacing is being delivered to the patient; a minimum value of the electrical activity over the cardiac cycle occurs within a selected minimum time window of a QRS complex time extending from an onset of a QRS complex within the electrical activity over the cardiac cycle to an offset of the xQRS complex; and a maximum value of the electrical activity over the cardiac cycle occurs within a selected maximum time window of the QRS complex time. Further, in one or more embodiments, the selected minimum time window may extend between 15% and 50% of the QRS complex time, and the selected maximum time window may extend between 50% and 85% of the QRS complex time.

Still further, in one or more embodiments, determining whether to correct the surrogate cardiac electrical activation time may include determining to correct the surrogate cardiac electrical activation time with late correction further if one or more of (e.g., one, some of, all, etc.): a magnitude of the maximum value of the electrical activity over the cardiac cycle relative a baseline value of the electrical activity is greater than a maximum threshold; a magnitude of the minimum value of the electrical activity over the cardiac cycle relative the baseline value of the electrical activity is greater than a minimum threshold; and a difference between the maximum value of the electrical activity and the minimum value of the electrical activity over the cardiac cycle is greater than a peak-to-peak threshold.

In one or more embodiments, determining whether to correct the surrogate cardiac electrical activation time may include determining to correct the surrogate cardiac electrical activation time with early correction if one or more of (e.g., one, some of, all, etc.): left ventricular cardiac pacing or biventricular cardiac pacing is being delivered to the patient; a difference between the maximum value of the electrical activity and the minimum value of the electrical activity over the cardiac cycle is less than a peak-to-peak threshold; a ratio of a magnitude of a minimum value of the electrical activity relative to a baseline value of the electrical activity over the cardiac cycle to a magnitude of a maximum value of the electrical activity relative to the baseline value of the electrical activity over the cardiac cycle is greater than a ratio threshold; the magnitude of the maximum value of the electrical activity relative to the baseline value over the cardiac cycle is less than a maximum threshold; and the minimum value occurs before the maximum value within the electrical activity over the cardiac cycle.

Further, in one or more embodiments, determining whether to correct the surrogate cardiac electrical activation time may include determining to correct the surrogate cardiac electrical activation time with early correction further if one or more of (e.g., one, some of, all, etc.): the minimum value does not occur within a selected onset time window of a QRS complex time extending from an onset of a QRS complex within the electrical activity over the cardiac cycle; and the maximum value does not occur within a selected offset time window of the QRS complex time extending to an offset of the QRS complex.

In one or more embodiments, determining whether to correct the surrogate cardiac electrical activation time may include determining to correct the surrogate cardiac electrical activation time with correlation correction if one or more of (e.g., one, some of, all, etc.): the morphology of electrical activity over the cardiac cycle monitored by a selected electrode is similar to the morphology of electrical activity over the cardiac cycle monitored by one or more electrodes located proximate to the selected electrode; and the surrogate cardiac electrical activation time generated from the electrical activity over the cardiac cycle monitored by a selected electrode is outside of a selected range from the median of the surrogate cardiac electrical activation times generated from the electrical activity monitored by the one or more electrodes located proximate to the selected electrode. Further, in one or more embodiments, the correction criterion defines a start time point and an end time point for the surrogate cardiac electrical activation time, and the end time point may correspond to a median end time point of the surrogate cardiac electrical activation times generated from the electrical activity monitored by the one or more electrodes located proximate to the selected electrode when regenerating the surrogate cardiac electrical activation time using correlation correction.

In one or more embodiments, the correction criterion defines a start time point and an end time point for the surrogate cardiac electrical activation time, and the end time point may be set to when the electrical activity is less than half of a maximum value of the electrical activity after occurrence of the maximum value of the electrical activity when regenerating the surrogate cardiac electrical activation time using late correction.

In one or more embodiments, the correction criterion defines a start time point and an end time point for the surrogate cardiac electrical activation time, and the end time point may be set to when the electrical activity is less than half of a minimum value of the electrical activity before occurrence of the minimum value of the electrical activity when regenerating the surrogate cardiac electrical activation time using early correction.

In one or more embodiments, the plurality of external electrodes may include surface electrodes positioned in an array configured to be located proximate the skin of the torso of the patient.

In one or more embodiments, activation times may be detected from each electrocardiogram (ECG) QRS complex based on a steepest, or maximum, negative deflection, or slope, within the QRS complex where onsets and offsets of each QRS complex may be automatically identified. Signals with multiple negative deflections may be more challenging to handle and time of steepest negative slope may shift from one deflection to the next based on noise or variations. The exemplary systems and methods may be described as providing robust processes of computing activation times based on restricting the search for steepest negative slope to certain fiducial points within the QRS complex based on amplitude and timing of negative valleys and positive peaks of each complex and/or correction of potential errors or outliers based on similarity of morphology of neighboring electrodes. Further, it may be described that the exemplary systems and methods provide improved ways of dealing with electrodes that may have erratic activation times due to multiple deflections and/or other issues.

The above summary is not intended to describe each embodiment or every implementation of the present disclosure. A more complete understanding will become apparent and appreciated by referring to the following detailed description and claims taken in conjunction with the accompanying drawings.

BRIEF DESCRIPTION OF THE DRAWINGS

FIGS. 8A-8B are another exemplary QRS complex of electrical activity over a cardiac cycle during intrinsic activity or right ventricular pacing depicting late activation time correction activation time determination and correction.

DETAILED DESCRIPTION OF EXEMPLARY EMBODIMENTS

Figure 1:
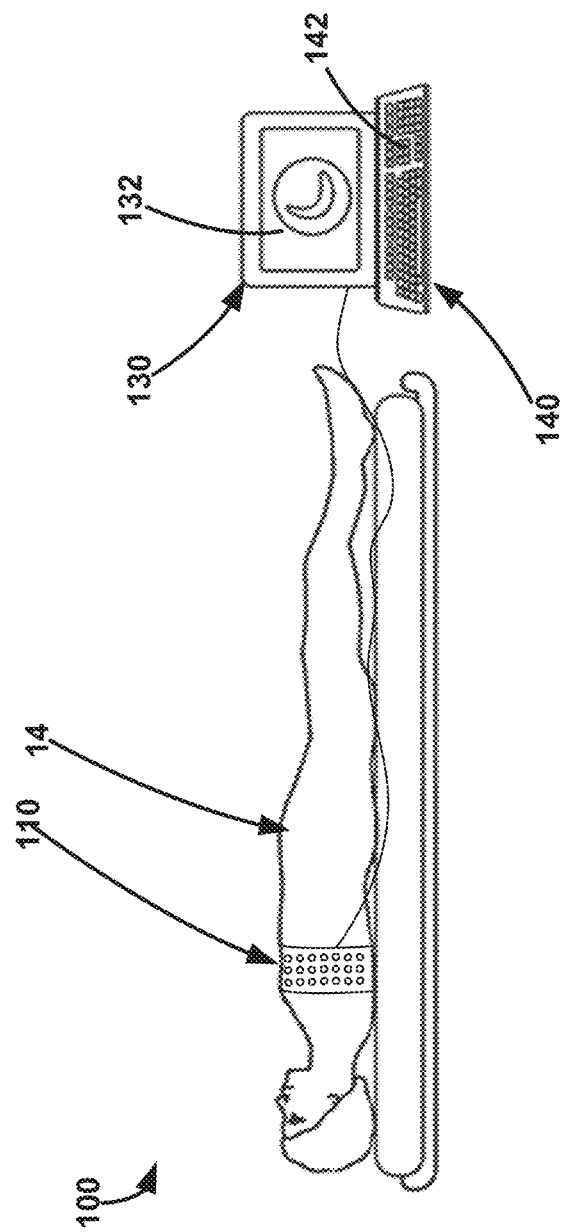
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods shall be described with reference to FIGS. 1-13. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Cardiac electrical activation times can be detected or estimated in proximity of a reference location (e.g., which can be a chosen location for a left ventricle lead during implant) using unipolar electrocardiogram (ECG) recordings. The cardiac electrical activation times may be used to generate electrical heterogeneity information that may be used by a user (e.g., physician) to optimize one or more settings, or parameters, of pacing therapy. Further, the electrical activation times may be measured and displayed, or conveyed, to a user by a system. As described herein, electrical activation times and/or electrical heterogeneity information may be used in noninvasive configuration (e.g., optimization, adjustment, etc.) of cardiac therapy.

Various exemplary systems and methods may be configured to use electrode apparatus including external electrodes, display apparatus, and computing apparatus to noninvasively assist a user (e.g., a physician) in the configuration (e.g., optimization) of cardiac therapy. Such exemplary systems and methods may monitor electrical activity from a patient's skin and generating surrogate cardiac electrical activation times from the electrical activity as will be described further herein. An exemplary system 100 including electrode apparatus 110, display apparatus 130, and computing apparatus 140 is depicted in FIG. 1.

The electrode apparatus 110 as shown includes a plurality of electrodes incorporated, or included, within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Exemplary electrode apparatus may be described in U.S. patent application Ser. No. 14/227,719 entitled Exemplary electrode apparatus may be described in U.S. Pat. No. 9,320,446 entitled "Bioelectric Sensor Device and Methods" filed Mar. 27, 2014 and issued on Mar. 26, 2016, which is incorporated herein by reference in its entirety. Further, exemplary electrode apparatus 110 will be described in more detail in reference to FIGS. 2-3.

Although not described herein, the exemplary system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the exemplary systems, methods, and interfaces described herein may further use imaging apparatus to provide noninvasive assistance to a user (e.g., a physician) to locate, or select, a pacing electrode or vector proximate the patient's heart in conjunction with the configuration of cardiac therapy.

For example, the exemplary systems, methods, and interfaces may provide image guided navigation that may be used to navigate leads including electrodes, leadless electrodes, wireless electrodes, catheters, etc., within the patient's body while also providing noninvasive cardiac therapy configuration including determining an effective, or optimal, pacing parameters such as A-V interval and V-V intervals. Exemplary systems and methods that use imaging apparatus and/or electrode apparatus may be described in U.S. Pat. App. Pub. No. 2014/0371832 to Ghosh published on Dec. 18, 2014, U.S. Pat. App. Pub. No. 2014/0371833 to Ghosh et al. published on Dec. 18, 2014, U.S. Pat. App. Pub. No. 2014/0323892 to Ghosh et al. published on Oct. 30, 2014, U.S. Pat. App. Pub. No. 2014/0323882 to Ghosh et al. published on Oct. 20, 2014, each of which is incorporated herein by reference in its entirety.

Exemplary imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MM), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate implantable apparatus to target locations within the heart or other areas of interest.

Systems and/or imaging apparatus that may be used in conjunction with the exemplary systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. No. 8,731,642 to Zarkh et al. issued on May 20, 2014, U.S. Pat. No. 8,861,830 to Brada et al. issued on Oct. 14, 2014, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), cardiac electrical activation times, one or more fiducial points, values, or times within electrical activity of a cardiac cycle, QRS complex, depolarization portion of the cardiac cycle, electrical heterogeneity information, etc. Electrical heterogeneity information, or electrical dyssynchrony information, may be representative of at least one of mechanical cardiac functionality and electrical cardiac functionality, surrogate electrical activation information or data, etc. that is generated using electrical signals gathered, monitored, or collected, using the electrode apparatus 110. The cardiac electrical activation times monitored, analyzed, and/or displayed may need correction, and thus, the computing apparatus 140 may be configured to determine which of the cardiac electrical activation times need correction, determine how to correct such cardiac electrical activation times, and then corrected such cardiac electrical activation times. More specifically, for example, one or more metrics such as, but not limited to, minimum values, maximum values, minimum slopes, maximum slopes, baseline values, early and late thresholds, QRS onsets, QRS offsets, etc. may be used to determine whether a cardiac electrical activation time needs correction. Further, such cardiac electrical activation times may be corrected using the same one or more metrics.

In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for analyzing a plurality of electrical signals captured by the electrode apparatus 110, for determining QRS onsets, QRS offsets, medians, modes, averages, peaks or maximum values, valleys or minimum values, for determining electrical activation times, for driving a graphical user interface configured to noninvasively assist a user in configuring one or more pacing parameters, or settings, such as, e.g., V-V interval, A-V interval, for driving a graphical user interface configured to noninvasively assist a user in selecting a pacing location before, during, or after implantation of an implantable medical device, etc.

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to view and/or select one or more pieces of configuration information related to the cardiac therapy.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including one or more pacing parameters, surrogate cardiac electrical activation times, electrical heterogeneity information, textual instructions, graphical depictions of electrical activation information, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, maximum and minimum value determinations, slope determinations, maximum and minimum slope determinations, comparison algorithms, vector mathematics, or any other processing required to implement one or more exemplary methods and/or processes described herein. Data stored and/or used by the computing apparatus 140 may include, for example, electrical signal/waveform data from the electrode apparatus 110, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, electrical heterogeneity information, etc.), or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, mini computer, tablet computer, etc.). The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes, or programs (e.g., the functionality provided by such systems, processes, or programs) described herein.

Figure 2:
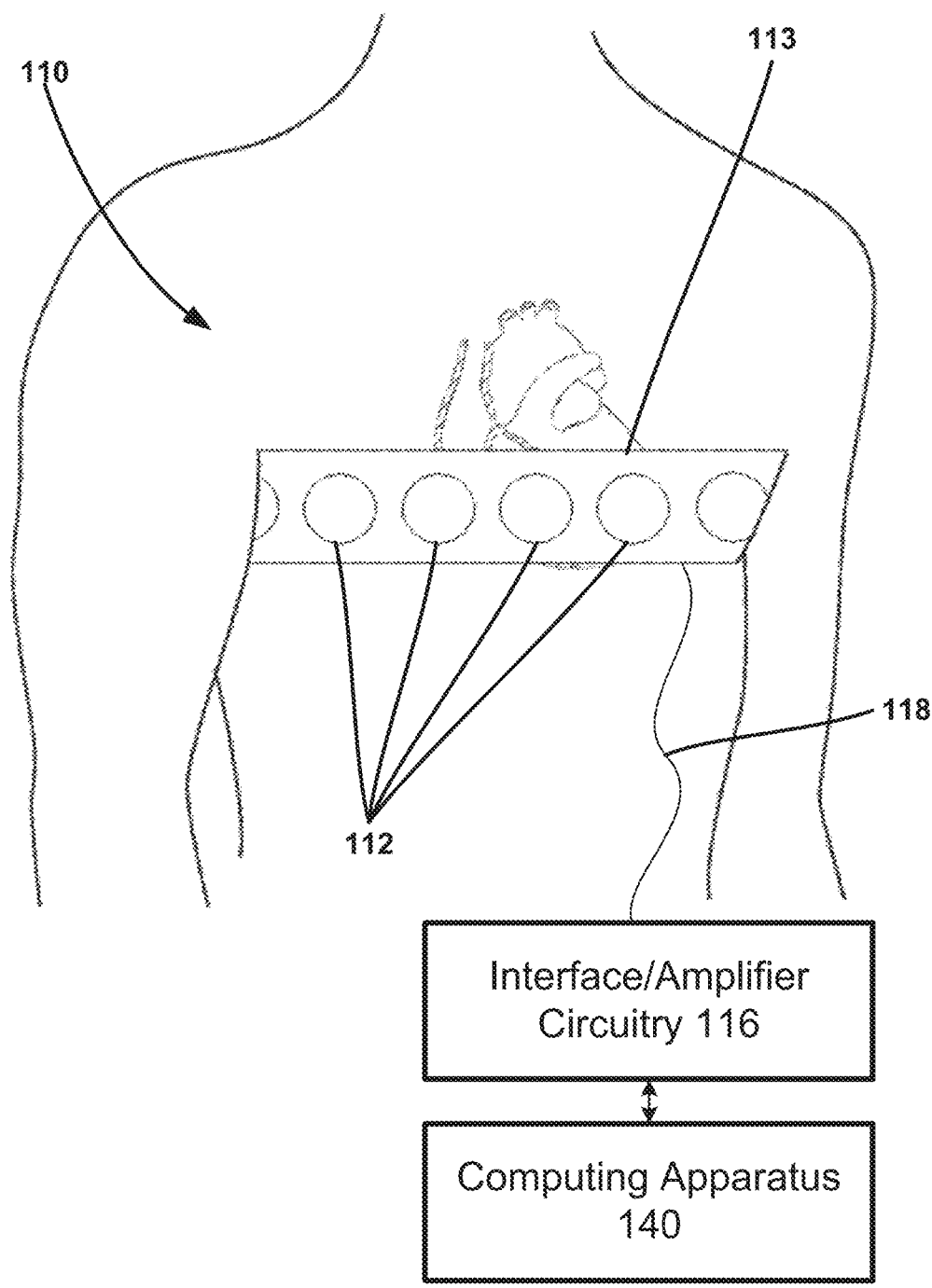
FIGS. 2-3 are diagrams of exemplary external electrode apparatus for measuring torso-surface potentials.

Electrical activation times of the patient's heart may be useful to evaluate cardiac therapy being delivered to a patient. Surrogate electrical activation information or data of one or more regions of a patient's heart may be monitored using electrode apparatus 110 as shown in FIG. 1 and in FIGS. 2-3. The exemplary electrode apparatus 110 may be configured to measure body-surface potentials of a patient 14 and, more particularly, torso-surface potentials of a patient 14. As shown in FIG. 2, the exemplary electrode apparatus 110 may include a set, or array, of electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 14. Further, in other examples, electrodes 112 (e.g., arranged in an array) may be part of, or located within, patches, vests, and/or other manners of securing the electrodes 112 to the torso of the patient 14. Still further, in other examples, the electrodes 112 may be part of, or located within, two sections of material or two "patches." One of the two sections or patches may be located on the anterior side of the torso of the patient 14 (to, e.g., monitor electrical signals representative of the anterior side of the patient's heart, measure surrogate cardiac electrical activation times representative of the anterior side of the patient's heart, etc.) and the other section or patch may be located on the posterior side of the torso of the patient 14 (to, e.g., monitor electrical signals representative of the posterior side of the patient's heart, measure surrogate cardiac electrical activation times representative of the posterior side of the patient's heart, etc.).

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of patient. Other configurations may have more or fewer electrodes 112.

The computing apparatus 140 may record and analyze the torso-surface potential signals sensed by electrodes 112 and amplified/conditioned by the interface/amplifier circuitry 116. The computing apparatus 140 may be configured to analyze the signals from the electrodes 112 to provide surrogate electrical activation information or data such as surrogate cardiac electrical activation times, e.g., representative of actual, or local, electrical activation times of one or more regions of the patient's heart as will be further described herein. In one or more embodiments, measurement of activation times can be performed by picking appropriate fiducial points (e.g., peak values, minimum values, minimum slopes, maximum slopes, zero crossings, threshold crossings, etc. of a near or far-field EGM) and measuring time between such fiducial points (e.g., within the electrical activity). For example, activation times may be generally determined by selecting the earliest onset time within electrical activity from a plurality of external electrodes over a cardiac cycle (e.g., a depolarization portion of the cardiac cycle, the QRS complex, etc.) to the steepest, or maximum, negative slope within the electrical activity monitored by the particular external electrode for which the activation time is being calculated for.

Additionally, the computing apparatus 140 may be configured to provide graphical user interfaces depicting the surrogate electrical activation times obtained using the electrode apparatus 110. Exemplary systems, methods, and/or interfaces may noninvasively use the electrical information collected using the electrode apparatus 110 to evaluate and configure cardiac therapy being delivered to the patient.

Figure 3:
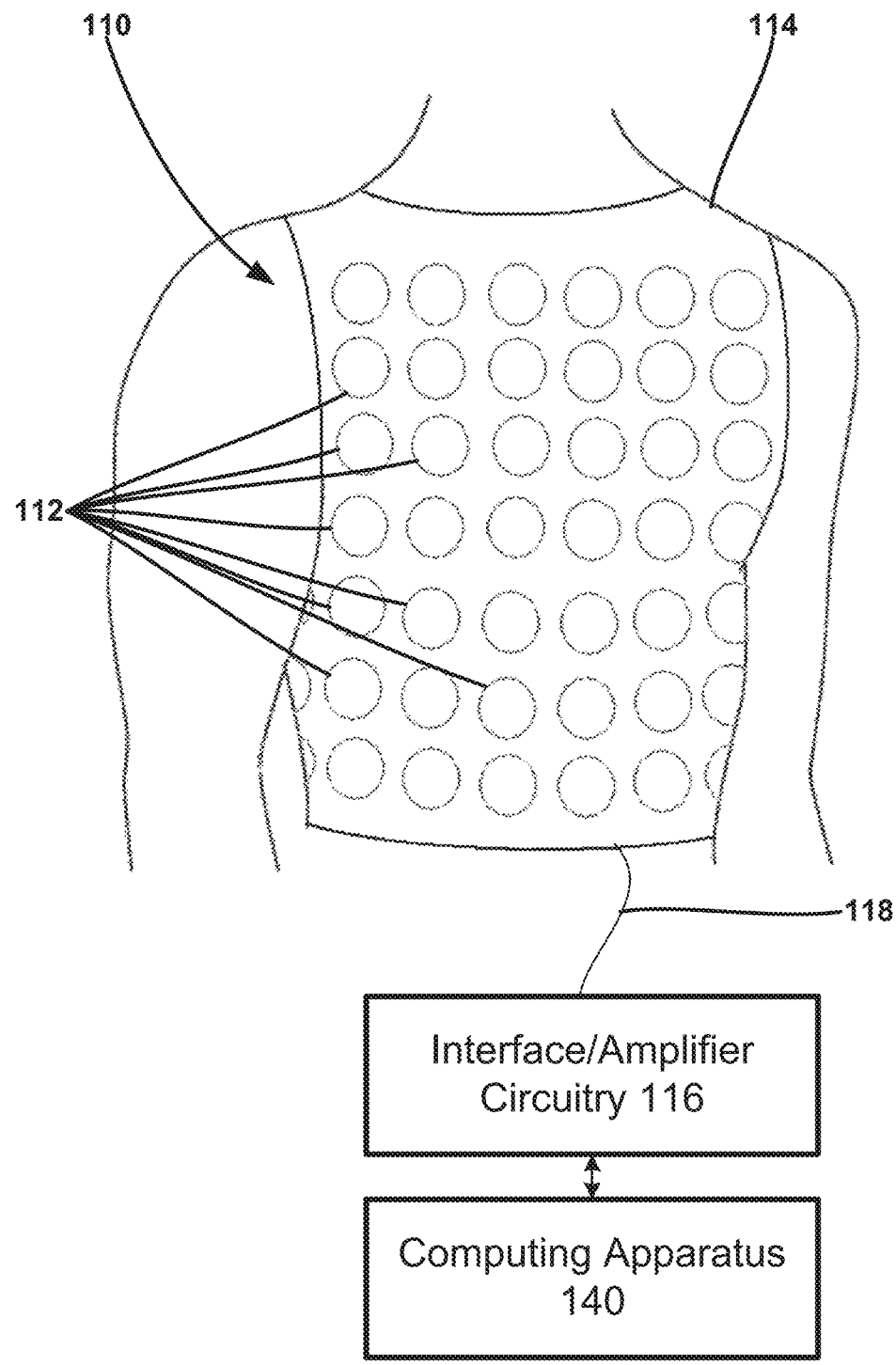

FIG. 3 illustrates another exemplary electrode apparatus 110 that includes a plurality of electrodes 112 configured to surround the heart of the patient 14 and record, or monitor, the electrical signals associated with the depolarization and repolarization of the heart after the signals have propagated through the torso of the patient 14. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 14, including, for example, the posterior, lateral, posterolateral, anterolateral, and anterior locations of the torso of a patient 14.

The vest 114 may be formed of fabric with the electrodes 112 attached to the fabric. The vest 114 may be configured to maintain the position and spacing of electrodes 112 on the torso of the patient 14. Further, the vest 114 may be marked to assist in determining the location of the electrodes 112 on the surface of the torso of the patient 14. In some examples, there may be about 25 to about 256 electrodes 112 distributed around the torso of the patient 14, though other configurations may have more or fewer electrodes 112.

As described herein, the electrode apparatus 110 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart.

The exemplary systems and methods may be used to provide noninvasive assistance to a user in the evaluation and configuration of cardiac therapy (e.g., cardiac therapy being presently-delivered to a patient during implantation or after implantation). To do so, the exemplary systems and methods may be monitor a plurality of electrical signals using a plurality of external electrodes proximate, or in contact, with the patient's skin, and then calculate, or determine, a surrogate cardiac electrical activation time for one or more of the plurality of external electrodes. Such surrogate cardiac electrical activation times may then be used to determine various metrics that may be used to provide noninvasive assistance to a user in the evaluation and configuration of cardiac therapy.

Figure 4:
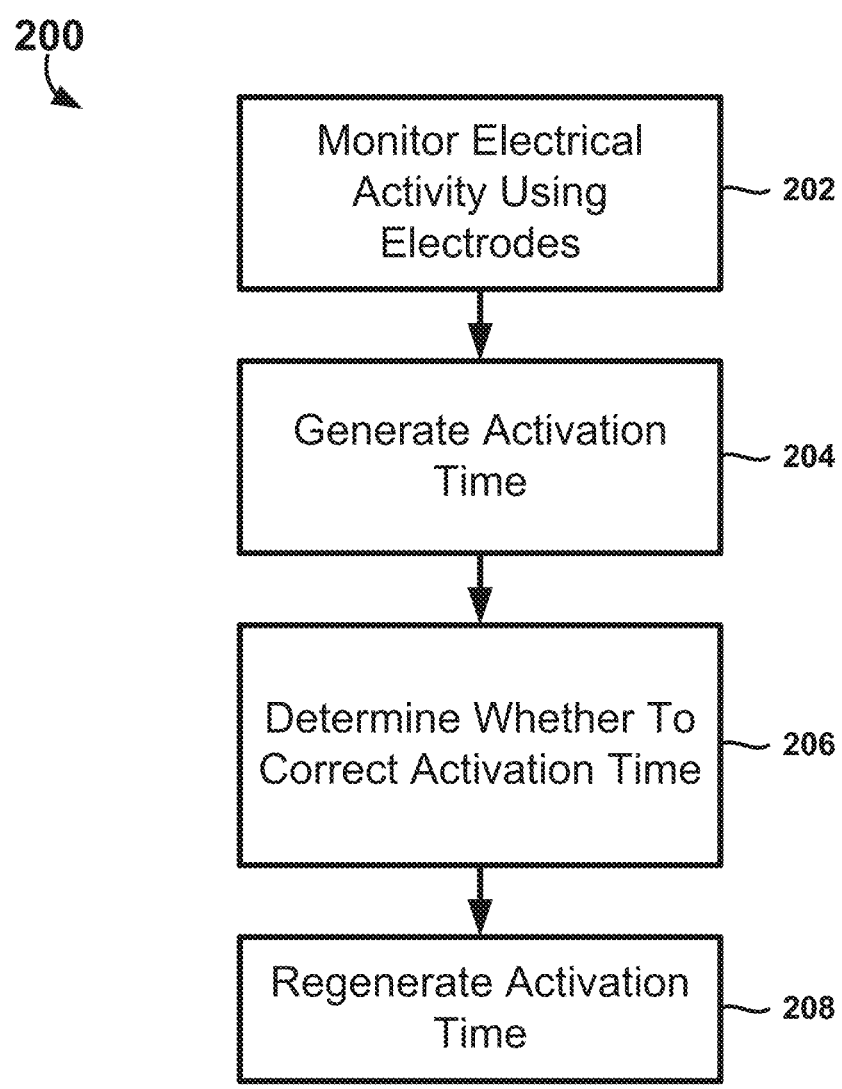
FIG. 4 is a block diagram of an exemplary method for generating activation times.

An exemplary method 200 for generating activation times is depicted in FIG. 4. As shown, the method 200 includes monitoring electrical activity using a plurality of electrodes 202. The plurality of electrodes may be external surface electrodes configured in a band or a vest similar to as described herein with respect to FIGS. 1-3. Each of the electrodes may be positioned or located about the torso of the patient so as to monitor electrical activity (e.g., acquire torso-potentials) from a plurality of different locations about the torso of the patient. Each of the different locations where the electrodes are located may correspond to the electrical activation of different portions or regions of cardiac tissue of the patient's heart.

The monitored electrical activity may be used to generate surrogate cardiac electrical activation times 204 for each of the plurality of electrodes. Generation of a surrogate cardiac electrical activation time for a particular electrode may be completed by analyzing the electrical activity of the particular electrode and/or the electrical activity of the other electrodes For example, in one or more embodiments, the electrical signals across all of the electrodes may be monitored and analyzed for the earliest occurring QRS onset for a cardiac cycle across all of the electrical signals (e.g., at least all of the electrical signals that are considered to be valid signals, at least all of the electrical signals that are being measured by electrodes in acceptable contact with the patient's skin, etc.). The time at which the earliest occurring QRS onset in a cardiac cycle (e.g., cardiac depolarization cycle) across all of the electrodes (and electrical signals) may be used as starting time point, or start time, for the computation, or calculation, of each of the surrogate cardiac electrical activation times.

The end time point, or end time, for a particular electrode may be determined using the electrical activity monitored by that particular electrode. For example, a fiducial point may be selected within the cardiac cycle, or more specifically, the cardiac depolarization cycle (e.g., QRS complex, time period between QRS onset and QRS offset) of the electrical activity of the particular electrode. The time at which the fiducial point, or value, occurs within the cardiac cycle may set, or define, the end time point of the activation time for the particular electrode.

In one or more embodiments, the fiducial point used as the end time point for calculation of surrogate cardiac electrical activation time is related to the steepest, or maximum, negative slope of the electrical activity of the cardiac depolarization cycle (e.g., QRS complex, time period between QRS onset and QRS offset). More specifically, for example, the fiducial point may be the first point that is within 10% of the steepest, or maximum, negative slope of the electrical activity of the cardiac depolarization. Exemplary systems and methods of determining QRS onsets, QRS offsets, activation time end points, etc. is described within U.S. Pat. No. 9,132,274 entitled "DETERMINING ONSETS AND OFFSETS OF CARDIAC DEPOLARIZATION AND REPOLARIZATION WAVES" and issued on Sep. 15, 2015, which is incorporated by reference herein in its entirety.

Regardless of the typical, or default, process that each of the surrogate cardiac electrical activation times is generated, the typical, or default, process may be described as using baseline criterion. In other words, the standard way of generating, or calculating, the surrogate cardiac electrical activation times may use baseline criterion. In the example above, the baseline criterion may define a start time point and an end time point for the surrogate cardiac electrical activation time. The start time may be the earliest QRS onset from the electrical activity monitored across all of the plurality of electrodes. The end time point may be related to, or actually is, the time at which the maximum negative slope occurs within the electrical activity over the cardiac depolarization cycle (e.g., QRS complex).

Thus, a surrogate cardiac electrical activation time or a plurality of surrogate cardiac electrical activation times may be generated 204 using the baseline criterion based on the electrical activity monitored using the plurality of electrodes. As noted herein, each of the electrodes, and corresponding electrical activity or signal, may have a surrogate cardiac electrical activation time generated. In other words, each electrode may have their own surrogate cardiac electrical activation time associated therewith. However, some of the generated surrogate cardiac electrical activation times may qualify for, or need to be, corrected due to various reasons such as, e.g., poor signal, signal artifacts, anomalies, outliers, noise, variations, low-amplitude fusion signals with two descending phases, signals with linear descending phase (slope is nearly constant), any of the preceding reasons accentuated by low amplitude signal combined with or separate from QR morphology any of the preceding reasons exacerbated by and/or due to imperfect onset/offset placement, etc. Further, low amplitude signals may result from characteristics of a waveform where multiple conduction wavefronts converge (e.g., during left or biventricular pacing).

To identify the surrogate cardiac electrical activation times to correct, the exemplary method 200 further includes determining whether a surrogate cardiac electrical activation time qualifies for correction 206, and if the activation time qualifies for correction, then regenerating the activation time 208 based on correction criterion (as opposed to the baseline criterion used by the standard, or default, way of determining surrogate cardiac electrical activation times). The correction criterion may be different from the baseline criterion that may be typically (e.g., default) used to generate activation times, and may be designed, or configured, to correct any issues in the activation times that arose from using the baseline criterion.

In one or more examples of the correction criterion, the start time point may be the same as the baseline criterion, e.g., the earliest QRS onset time from a plurality of electrical signals monitored by a plurality of electrodes at different electrodes. In one or more other examples of the correction criterion, the start time point may be different than the baseline criterion's start time point. In one or more embodiments such as the following embodiments described herein, the end time point, or end time, of the corrected criterion may be different than the baseline criterion's end time point.

Figure 5:
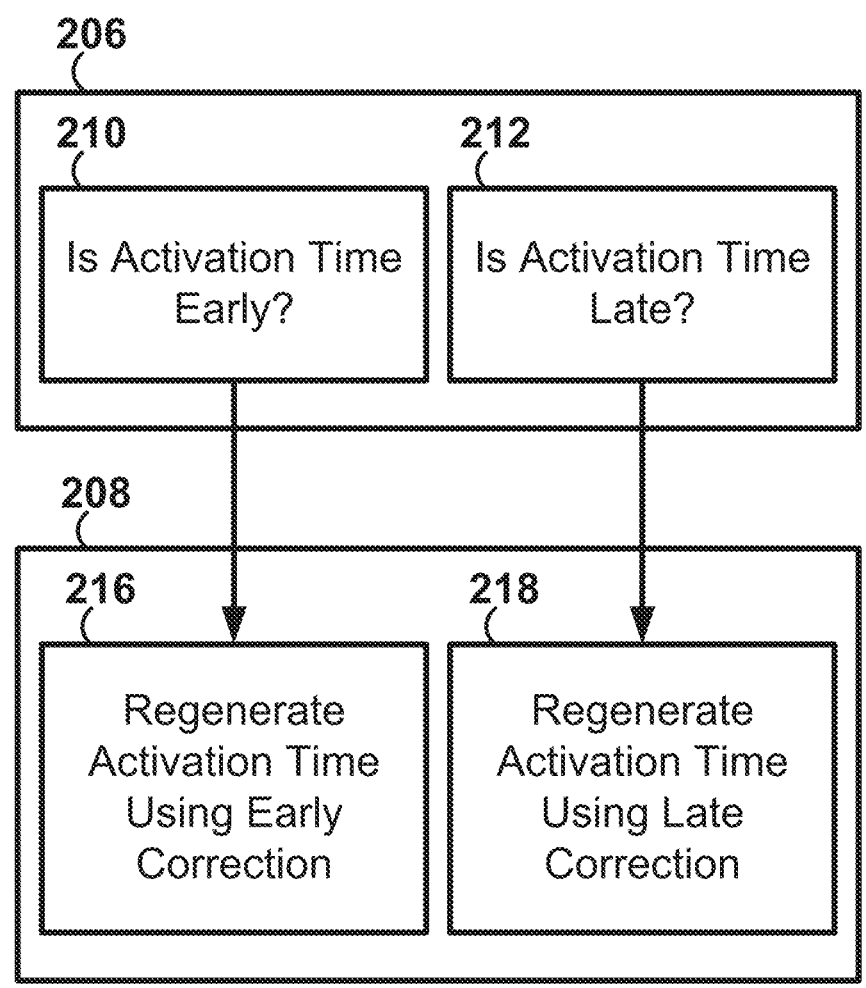
FIG. 5 is a detailed block diagram of a few processes of the exemplary method of FIG. 4.

In at least one embodiment as shown in FIG. 5, determining whether to correct a surrogate cardiac electrical activation time 206 may include determining whether the activation time is early 210 or whether the activation time is late 212. Then, depending on whether the activation time is early or late, regenerating the activation time 208 may use either early correction criterion 216 or late correction criterion 218.

Figure 6:
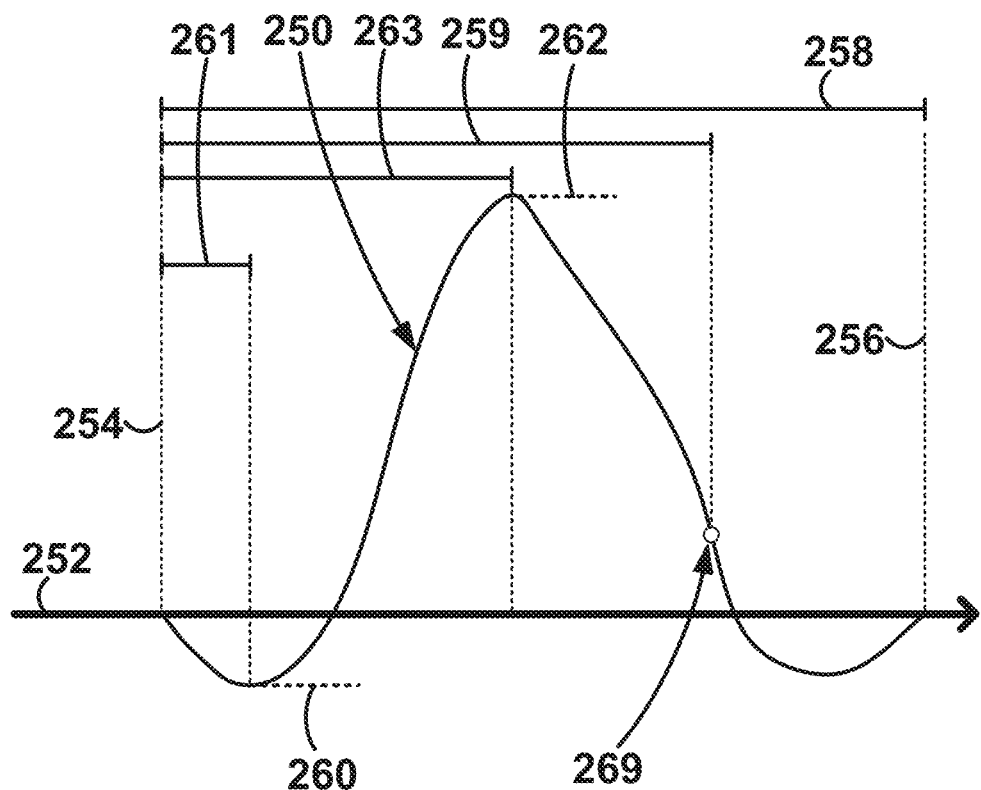
FIG. 6 is an exemplary QRS complex of electrical activity over a cardiac cycle.

Examples of determining whether to correction an activation time 206, and then correcting the activation time in response to a determination to correct the activation time are depicted in FIGS. 6-10. As described herein, a plurality of different metrics may be used to determine whether to correct an activation time 206 (e.g., whether the activation time qualifies for correction). An exemplary QRS complex of electrical activity over a cardiac cycle is depicted in FIG. 6 including illustrations of many metrics that may be used to determine whether to correct an activation time 206.

As shown, a portion of an electrical signal, or electrical activity, 250 is plotted on along a time axis 252. The portion of the electrical signal 250 in this example is a QRS complex extending from a QRS onset time 254 to a QRS offset time 256 defining a QRS time window 258. The axis 252 is vertically adjusted so be represent a baseline value for the electrical signal. The baseline value may be the signal value immediately prior to onset of the QRS complex. In one or more embodiments, the baseline value may be 0 millivolts or close to 0 millivolts.

A minimum value, or Q, 260 may be determined, and the time period extending from the QRS onset time 254 to the minimum value 260 may be referred to as the minimum time period, or QT, 261. Similarity, a maximum value, or R, 262 may be determined, and the time period extending from the QRS onset time 254 to the maximum value 262 may be referred to as the minimum time period, or RT, 263.

As described herein, activation time, or AT, 259 may be determined from the earliest QRS onset time 254 to a point related to the steepest negative slope 269 (e.g., the first point within 10% of the steepest negative slope, the point at the steepest negative slope, etc.). Only a single electrical signal, or electrical activity, 250 is depicted in each of FIGS. 6-10, and even though the QRS onset time 254 depicted may or may not be the earliest QRS onset time from a plurality of electrical signals monitored by a plurality of electrodes, it is to be understood that the QRS onset time 254 shown in each of the figures will be used for determining activation time 259 as described herein. In other words, it may be assumed that the QRS onset time 254 depicted in each of FIGS. 6-10 is the earliest QRS onset time among a plurality of QRS onset times within multiple electrical signals monitored by a plurality of electrodes.

Figure 7A:
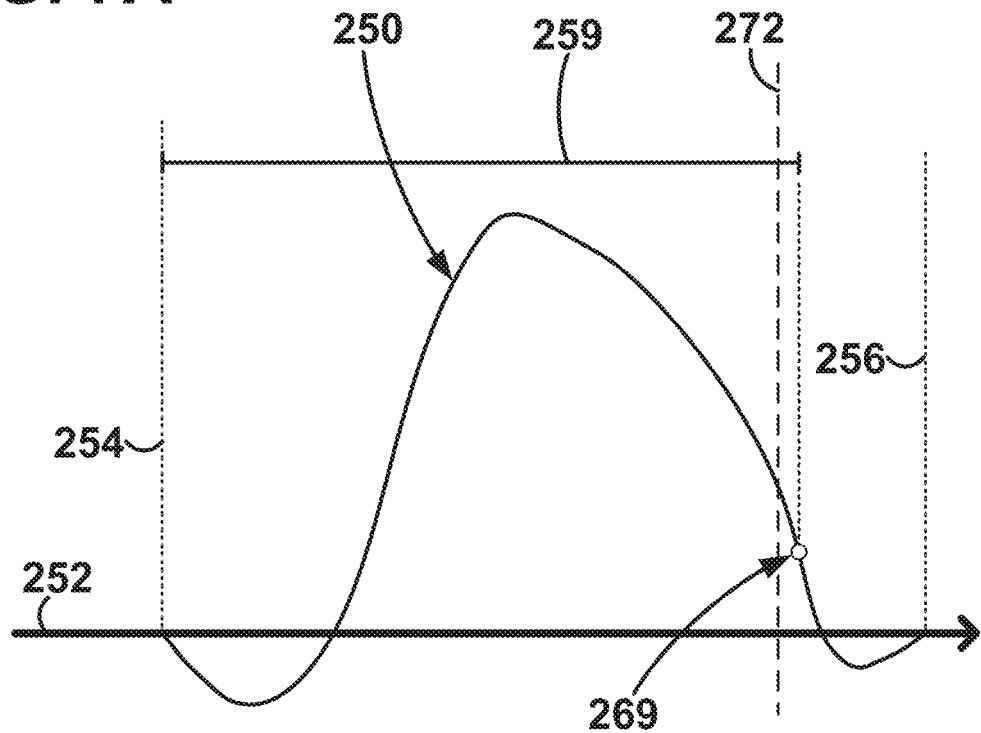
FIGS. 7A-7B are an exemplary QRS complex of electrical activity over a cardiac cycle depicting late activation time correction activation time determination and correction.

An exemplary QRS complex of electrical activity 250 over a cardiac cycle that qualities for, or is determined for correction using, late activation time correction activation time is depicted in FIG. 7A. As shown, the activation time 259 is generated from the QRS onset time 254 to the steepest negative slope 269 per baseline criterion.

The activation time 259 of electrical activity 250 of FIG. 7A may be evaluated to determine whether to correct the activation time 259 using, or with, late activation time correction. For example, it may be determined to correct the surrogate cardiac electrical activation time 259 using late correction if the surrogate cardiac electrical activation time 259 is greater than or equal to a selected late correction threshold 272. As shown in FIG. 7A, the activation time 259 is greater than or equal to a selected late correction threshold 272, and thus, the activation time 259 is determined to be qualified for late correction.

The late correction threshold 272 may be a percentage or ratio of the QRS time window 258, which extends from the QRS onset 254 to the QRS offset 256. As shown in FIG. 7A, the late correction threshold 272 is about 80% of the QRS time window 258. Further, for example, the late correction threshold 272 may be greater than or equal to about 70% of the QRS time window 258, greater than or equal to about 75% of the QRS time window 258, greater than or equal to about 80% of the QRS time window 258, greater than or equal to about 85% of the QRS time window 258, etc. Further, the selected late correction threshold 272 may depend on what, if any, pacing is being delivered to the patient. In at least one embodiment, the late correction threshold 272 may be 80% of the QRS time window 258 for intrinsic rhythms. Further, in at least one embodiment, the late correction threshold 272 may be 75% of the QRS time window 258 for paced rhythms.

Figure 7B:
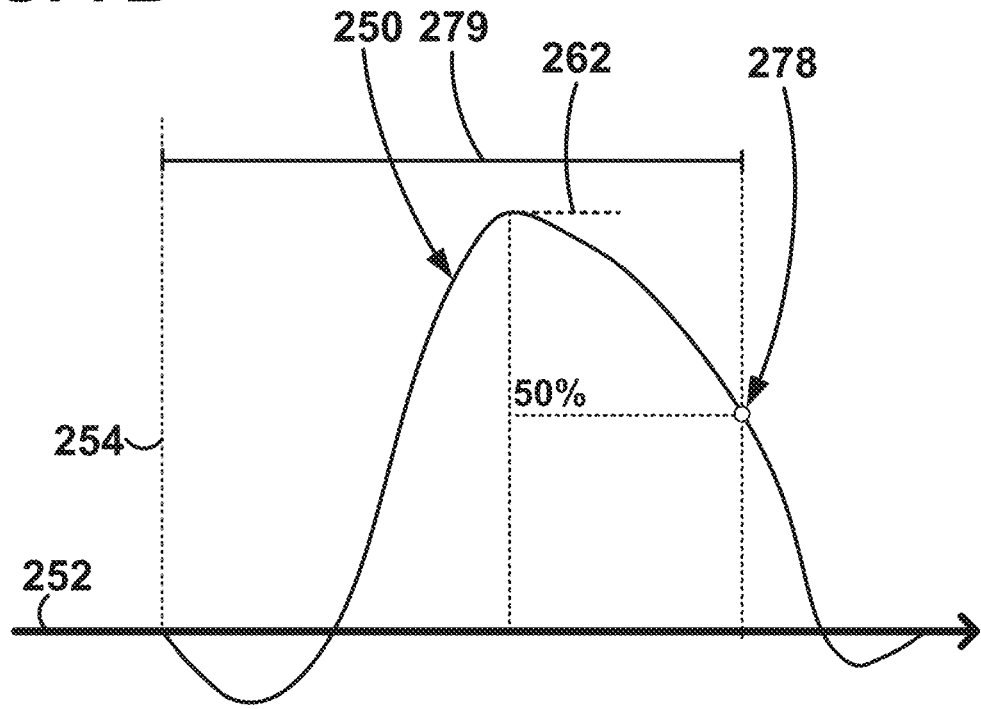

Since the activation time 259 of FIG. 7A is determined to be corrected using, or qualified for, late correction, the activation time 279 may be regenerated according to late correction criterion as depicted in FIG. 7B. The late correction criterion may define a start time point as the earliest QRS onset 254 similar to the baseline criterion and may define an end time point that is different from the baseline criterion. In this example, the end time point 278 may be set to when the electrical activity 250 is less than half of a maximum value 262 of the electrical activity 250 after, or following, the occurrence of the maximum value 262 thereby defining a regenerated activation time 279 as depicted. As shown in this example, the regenerated activation time 279 is shorter than the initially generated activation time 259.

An exemplary QRS complex of electrical activity 250 over a cardiac cycle during intrinsic activity or right ventricular pacing that qualities for, or is determined for correction using, late activation time correction is depicted in FIG. 8A. As shown, the activation time 259 is generated from the QRS onset time 254 to the steepest negative slope 269 per baseline criterion.

The activation time 259 of electrical activity 250 of FIG. 8A may be evaluated to determine whether to correction the activation time 259 using late correction. For example, it may be determined to correct the surrogate cardiac electrical activation time 259 if one or more (e.g., one, some of, all, etc.) of the following conditions occur or are present: right ventricular cardiac pacing or no cardiac pacing is being delivered to the patient, a minimum value 260 of the electrical activity 250 occurs within a selected minimum time window extending from line 280 to line 282, and a maximum value 262 of the electrical activity 250 occurs within a selected maximum time window extending from line 282 to line 284. In at least one embodiment, the selected minimum time window extends between about 15% and about 50% of the QRS complex time 258, and the selected maximum time window extends between about 50% and about 85% of the QRS complex time 258.

Additionally, the late correction criterion in this example may further include determining whether the magnitudes of the maximum and minimum values 260, 262 exceed a low threshold and/or whether a difference between magnitudes of the maximum and minimum values 260, 262 exceeds a threshold value. For example, it may be determined to correct the activation time 259 if one or more (e.g., one, some of, all, etc.) of the following conditions occur or are present: a magnitude of the maximum value 262 of the electrical activity 250 relative the baseline value 252 is greater than a maximum threshold, a magnitude of the minimum value 260 of the electrical activity 250 relative the baseline value 252 is greater than a minimum threshold, and a difference between the maximum value 262 and the minimum value 260 over the cardiac cycle is greater than a peak-to-peak threshold.

In at least one embodiment, the maximum threshold may be 0.1 millivolts. In at least one embodiment, the minimum threshold may be 0.1 millivolts. Further, for example, one or both of the maximum thresholds may be greater than or equal to about 0.025 millivolts, greater than or equal to about 0.05 millivolts, greater than or equal to about 0.15 millivolts, greater than or equal to about 0.2 millivolts, etc. and/or less than equal to about 0.3 millivolts, less than equal to about 0.25 millivolts, less than equal to about 0.175 millivolts, less than equal to about 0.125 millivolts, etc. In at least one embodiment, the peak-to-peak threshold may be 0.4 millivolts. Further, for example, the peak-to-peak threshold may be greater than or equal to about 0.2 millivolts, greater than or equal to about 0.25 millivolts, greater than or equal to about 0.3 millivolts, greater than or equal to about 0.35 millivolts, etc. and/or less than equal to about 0.6 millivolts, less than equal to about 0.5 millivolts, less than equal to about 0.45 millivolts, less than equal to about 0.325 millivolts, etc.

Still further, the late correction criterion in this example may further include determining whether the minimum value 260 occurred before the maximum value. In other words, whether the minimum time 261 is less than the maximum time 262.

As shown in FIG. 8A, the minimum time, or TQ, 261 is within the minimum time window between line 280 and line 282 and the maximum time, or TR, 263 is within the maximum time window between line 282 and line 284, both the minimum and maximum values 260, 262 are greater than the minimum and maximum thresholds, the difference between the minimum and maximum values 260, 262 is less that the peak-to-peak threshold, and the minimum value 260 occurred before the maximum value, and thus, the activation time 259 is determined to be qualified for late activation time correction.

Since the activation time 259 of FIG. 8A is determined for correction using late activation time correction, the activation time 279 may be regenerated according to late correction criterion as depicted in FIG. 8B similar to as shown in FIG. 7B. As shown, in this example, the end time point 278 may be set to when the electrical activity 250 is less than half of a maximum value 262 of the electrical activity 250 after occurrence of the maximum value 262 thereby defining a regenerated activation time 279 as depicted. As shown in this example, the regenerated activation time 279 is shorter than the initially generated activation time 259.

Figure 9A:
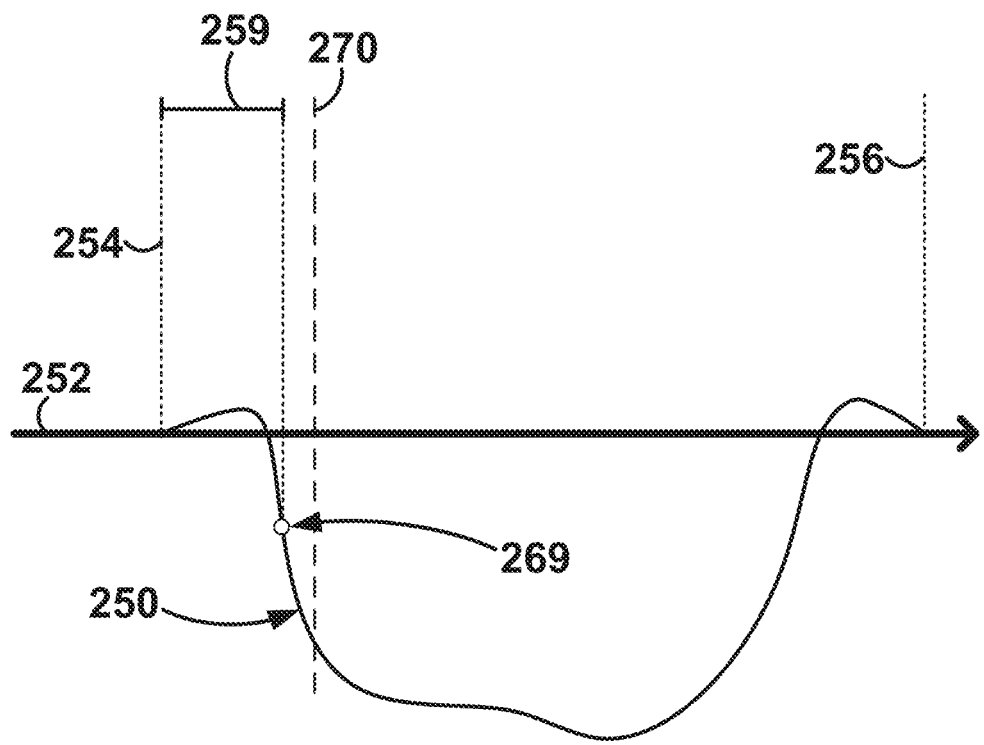
FIGS. 9A-9B are an exemplary QRS complex of electrical activity over a cardiac cycle depicting early activation time determination and correction.

An exemplary QRS complex of electrical activity 250 over a cardiac cycle that qualities for, or is determined to be corrected using, early activation time correction is depicted in FIG. 9A. As shown, the activation time 259 is generated from the QRS onset time 254 to the steepest negative slope 269 per baseline criterion.

The activation time 259 of electrical activity 250 of FIG. 9A may be evaluated to determine whether to correction the activation time 259. For example, it may be determined to correct the surrogate cardiac electrical activation time 259 using, or with, early activation time correction if the surrogate cardiac electrical activation time 259 is less than or equal to a selected early correction threshold 270. As shown in FIG. 9A, the activation time 259 is less than or equal to a selected early correction threshold 270, and thus, the activation time 259 is determined to be qualified for early correction.

The early correction threshold 270 may be a percentage or ratio of the QRS time window 258, which extends from the QRS onset 254 to the QRS offset 256. As shown in FIG. 9A, the early correction threshold 270 is about 20% of the QRS time window 258. Further, for example, the early correction threshold 270 may be less than or equal to about 40% of the QRS time window 258, less than or equal to about 35% of the QRS time window 258, less than or equal to about 30% of the QRS time window 258, less than or equal to about 25% of the QRS time window 258, less than or equal to about 15% of the QRS time window 258, etc. Further, the selected early correction threshold 270 may depend on what, if any, pacing is being delivered to the patient. In at least one embodiment, the early correction threshold 270 may be 20% of the QRS time window 258 for intrinsic rhythms. Further, in at least one embodiment, the early correction threshold 270 may be 25% of the QRS time window 258 for paced rhythms.

Figure 9B:
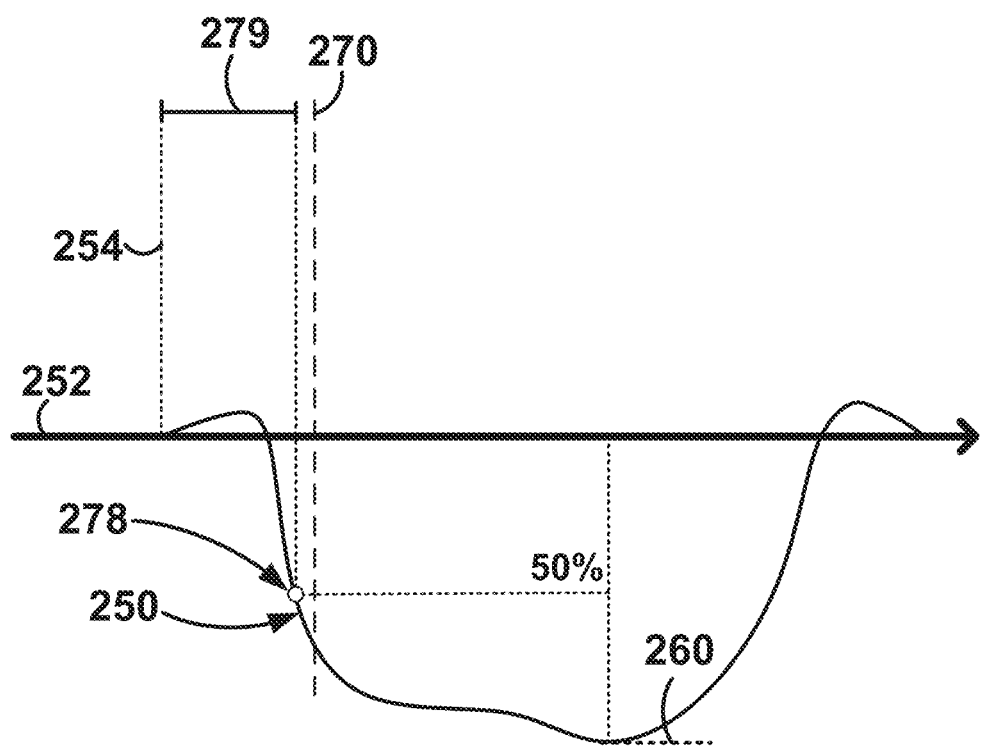

Since the activation time 259 of FIG. 9A is determined to be qualified for, or to be corrected using, early activation time correction, the activation time 279 may be regenerated according to early correction criterion as depicted in FIG. 9B. The early correction criterion may define a start time point as the earliest QRS onset 254 similar to the baseline criterion and may define an end time point that is different from the baseline criterion. In this example, the end time point 278 may be set to when the electrical activity 250 is less than half of a minimum value 260 of the electrical activity 250 after, or following, the QRS onset 254 to the minimum value 260 thereby defining a regenerated activation time 279 as depicted. As shown in this example, the regenerated activation time 279 is longer than the initially generated activation time 259.

Figure 10A:
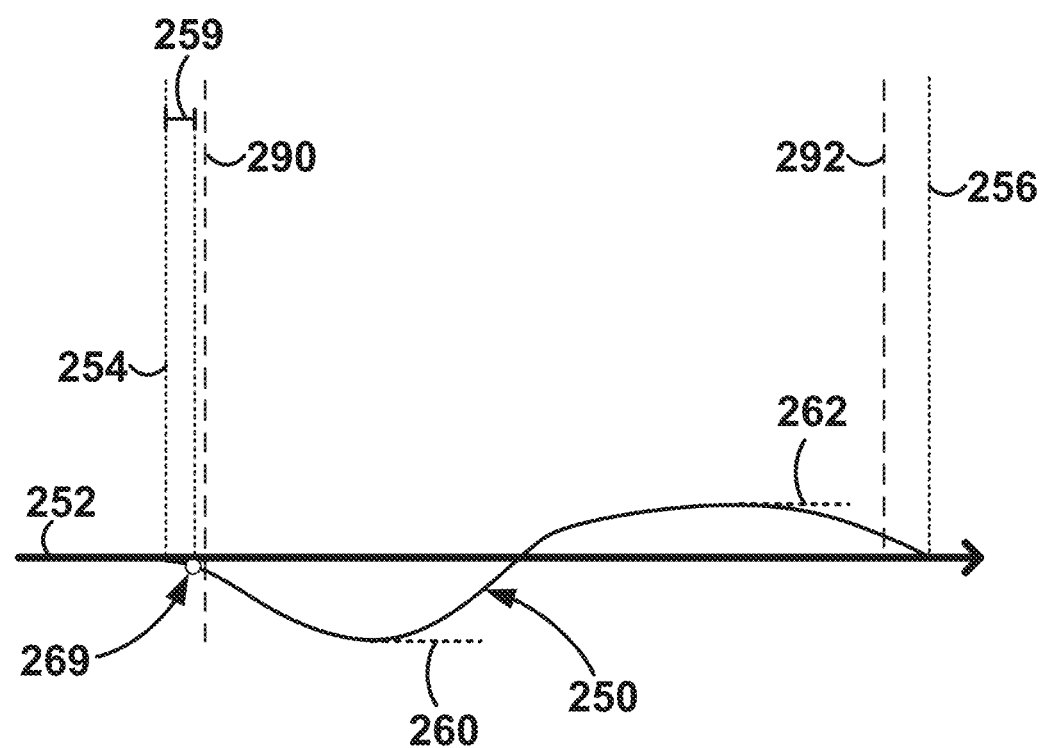
FIGS. 10A-10B are an exemplary QRS complex of electrical activity over a cardiac cycle during fusion activity from left ventricular or biventricular pacing depicting early activation time determination and correction.

An exemplary QRS complex of electrical activity 250 over a cardiac cycle during fusion activity from left ventricular or biventricular pacing that qualities for, or is determined to correct using, early activation time correction is depicted in FIG. 10A. As shown, the activation time 259 is generated from the QRS onset time 254 to the steepest negative slope 269 per baseline criterion.

The activation time 259 of electrical activity 250 of FIG. 10A may be evaluated to determine to correct the activation time 259 using, or with, early activation time correction. For example, it may be determined that the surrogate cardiac electrical activation time 259 qualifies for early activation time correction if one or more (e.g., one, some of, all, etc.) of the following conditions occur or are present: left ventricular cardiac pacing or biventricular cardiac pacing is being delivered to the patient, a difference between the maximum value 262 of the electrical activity 250 and the minimum value 260 of the electrical activity 250 over the cardiac cycle is less than a peak-to-peak threshold, a ratio of a magnitude of a minimum value 260 relative to a baseline value 252 to a magnitude of a maximum value 262 relative to the baseline value 252 is greater than a ratio threshold, the magnitude of the maximum value 262 relative to the baseline value 252 is less than a maximum threshold, and the minimum value 260 occurs before the maximum value 262 within the electrical activity 250 over the cardiac cycle.

In at least one embodiment, the peak-to-peak threshold may be about 0.5 millivolts. In other embodiments, the peak-to-peak threshold may be greater than or equal to about 0.25 millivolts, greater than or equal to about 0.3 millivolts, greater than or equal to about 0.4 millivolts, greater than or equal to about 0.475 millivolts, etc. and/or less than or equal to about 0.8 millivolts, less than or equal to about 0.7 millivolts, less than or equal to about 0.6 millivolts, less than or equal to about 0.55 millivolts, less than or equal to about 0.45 millivolts, etc.

In at least one embodiment, the ratio threshold may be about 0.12. In other embodiments, the ratio threshold may be greater than or equal to about 0.05, greater than or equal to about 0.075, greater than or equal to about 0.09, greater than or equal to about 0.1, etc. and/or less than or equal to about 0.2, less than or equal to about 0.175, less than or equal to about 0.15, etc.

In at least one embodiment, the maximum threshold may be about 0.32 millivolts. In other embodiments, the ratio threshold may be greater than or equal to about 0.2 millivolts, greater than or equal to about 0.25 millivolts, greater than or equal to about 0.3 millivolts, etc. and/or less than or equal to about 0.5 millivolts, less than or equal to about 0.4 millivolts, less than or equal to about 0.35 millivolts, etc.

Additionally, the early correction criterion in this example may further include determining whether the minimum value 260 does not occur within a selected onset time window of a QRS complex time 258 extending from an onset 254 of a QRS complex to an onset initial sample time 290 and the maximum value 262 does not occur within a selected offset time window of the QRS complex time extending from an offset initial sample time 292 to an offset of the QRS complex 256. The selected onset and offset time windows may extend a selected percentage, a selected amount of time, and/or a selected amount, or number, of samples. In at least one embodiment, one or both of the selected onset and offset time windows may extend for five samples (which may be about 5 milliseconds). In other embodiments, one or both of the selected onset and offset time windows may extend for greater than or equal to about 2 milliseconds, greater than or equal to about 3 milliseconds, greater than or equal to about 4 milliseconds, greater than or equal to about 5.5 milliseconds, etc. and/or less than or equal to about 10 milliseconds, less than or equal to about 8 milliseconds, less than or equal to about 7 milliseconds, less than or equal to about 6 milliseconds, less than or equal to about 4.5 milliseconds, etc.

As shown in FIG. 10A, left ventricular cardiac pacing or biventricular cardiac pacing is being delivered to the patient, a difference between the maximum value 262 of the electrical activity 250 and the minimum value 260 of the electrical activity 250 over the cardiac cycle is less than a peak-to-peak threshold, a ratio of a magnitude of a minimum value 260 relative to a baseline value 252 to a magnitude of a maximum value 262 relative to the baseline value 252 is greater than a ratio threshold, the magnitude of the maximum value 262 relative to the baseline value 252 is less than a maximum threshold, and the minimum value 260 occurs before the maximum value 262 within the electrical activity 250 over the cardiac cycle, and thus, the activation time 259 is determined to be qualified for early activation time correction.

Figure 10B:
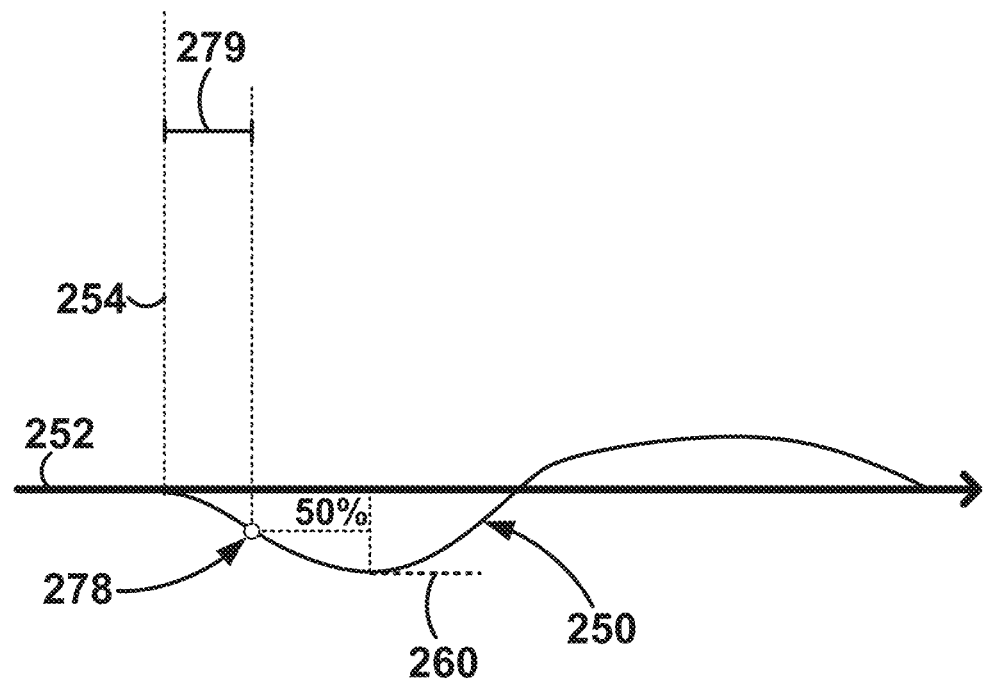

Since the activation time 259 of FIG. 10A is determined to be qualified for early correction, the activation time 279 may be regenerated according to early correction criterion as depicted in FIG. 10B similar to as shown in FIG. 9B. As shown, in this example, the end time point 278 may be set to when the electrical activity 250 is less than half of a minimum value 260 of the electrical activity 250 after the QRS onset 254 to the minimum value 260 thereby defining a regenerated activation time 279 as depicted. As shown in this example, the regenerated activation time 279 is longer than the initially generated activation time 259.

Additionally, the exemplary systems and methods may determine whether to correct a surrogate cardiac electrical activation based on morphology of the electrical activity within the cardiac cycle monitored by a particular electrode when compared to one or more other morphologies of the electrical activity within the cardiac cycle monitored by electrodes that are positioned proximate the particular electrode. For example, if the morphology of the electrical activity over the cardiac cycle monitored by a selected electrode is similar to the morphology of electrical activity over the cardiac cycle monitored by one or more electrodes located proximate to the selected electrode and the surrogate cardiac electrical activation time generated from the electrical activity over the cardiac cycle monitored by a selected electrode is outside of a selected range from the median of the surrogate cardiac electrical activation times generated from the electrical activity monitored by the one or more electrodes located proximate to the selected electrode, then the surrogate cardiac electrical activation time may be determined to be corrected or qualified for correction.

Correction in response to determination to correction based on morphology may utilize electrical activation time information from proximate electrodes. For example, the surrogate cardiac electrical activation time may be corrected by changing the end point of the activation time to a median, or another statistical metric, of surrogate cardiac electrical activation times generated from the electrical activity monitored by the one or more electrodes located proximate to the selected electrode.

In one embodiment, the morphology determination and correction by described as identifying potential errors/outliers in activation times, especially, for electrodes with low amplitudes (e.g., R-to-Q if less than 0.5 mV). More specifically, for example, starting with activation times from electrodes 1, 2, 3 . . . where electrode i is next in physical space to electrode i+1, correlation may be computed, or calculated, between the QRS complex of electrode i and electrode i+1. If correlation greater than or equal to 0.8, then i and i+1 may be determined to be similar. This process may be repeated, or looped until correlation is less than 0.8, and then this group may be designated as a group, or set, of electrodes with similar QRS morphology. If activation times of any one electrode is far from the median by greater than 50 milliseconds (e.g., absolute value of the activation time(i))–median(set of electrodes) is greater than 50), the activation time may be corrected by setting it (e.g., the end point of the activation time) to the median value (e.g., median steepest negative slope, etc.). Next, after correction, the process may begin again from the electrode where correlation fell below 0.8 and repeat the same process till all electrodes are processed.

It is to be understood that the exemplary systems and methods may use one or more various ways to determine whether to correction a surrogate cardiac electrical activation other than those described with respect to FIGS. 6-10. Further, the exemplary systems and methods may use a plurality of different metrics from the electrical activity to determine which surrogate cardiac electrical activation times may qualify for correction.

For example, the exemplary systems and methods may be configured to determine the maximum value, or R, and its timing, or TR, and the determine the minimum value, or Q, and its timing, or TQ, within the onset and offset of each QRS complex for a given electrode channel. If one or more (e.g., one, some of, all) of the ratio of the minimum value to the maximum value is greater than 1.1 and the timing of the minimum value is less than 5 samples (e.g., 5 milliseconds) and the minimum value occurs before the maximum value, then the exemplary systems and methods may determine activation time as the time of steepest negative slope from the onset to the minimum value. Further, if one or more (e.g., one, some of, all) of the ratio of the minimum value to the maximum value is greater than 1.1 and the timing of the minimum value is less than 5 samples (e.g., 5 milliseconds) and the maximum value occurs before the minimum value, then the exemplary systems and methods may determine activation time as the time of steepest negative slope from the minimum value to the maximum value.

Further, if one or more (e.g., one, some of, all) of the ratio of the maximum value to the minimum value is greater than 1.1, the timing of the maximum values is greater than 5 samples (e.g., 5 milliseconds), the timing of the maximum value is less than the QRS offset minus 10 milliseconds, and the minimum value occurs before the maximum value, then the exemplary systems and methods may determine activation times as the time of steepest negative slope from the timing of the maximum value to QRS offset. Still further, if one or more (e.g., one, some of, all) of the ratio of the maximum value to the minimum value is greater than 1.1, the timing of the maximum values is greater than 5 samples (e.g., 5 milliseconds), the timing of the maximum value is less than the QRS offset minus 10 milliseconds, and the maximum value occurs before the minimum value, then the exemplary systems and methods may determine activation times as the time of steepest negative slope from the timing of the minimum value to timing of the maximum value.

For other cases in this example, activation time (e.g., the end point of the activation time) may be determined as the time of the steepest negative slope from QRS onset to QRS offset.

The exemplary systems, methods, and graphical user interfaces described herein may be used with respect to the implantation and configuration of an implantable medical device (IMD) and/or one or more leads configured to be located proximate one or more portions of a patient's heart. For example, the exemplary systems, methods, and interfaces may be used in conjunction with an exemplary therapy system 10 described herein with reference to FIGS. 11-13.

Figure 11:
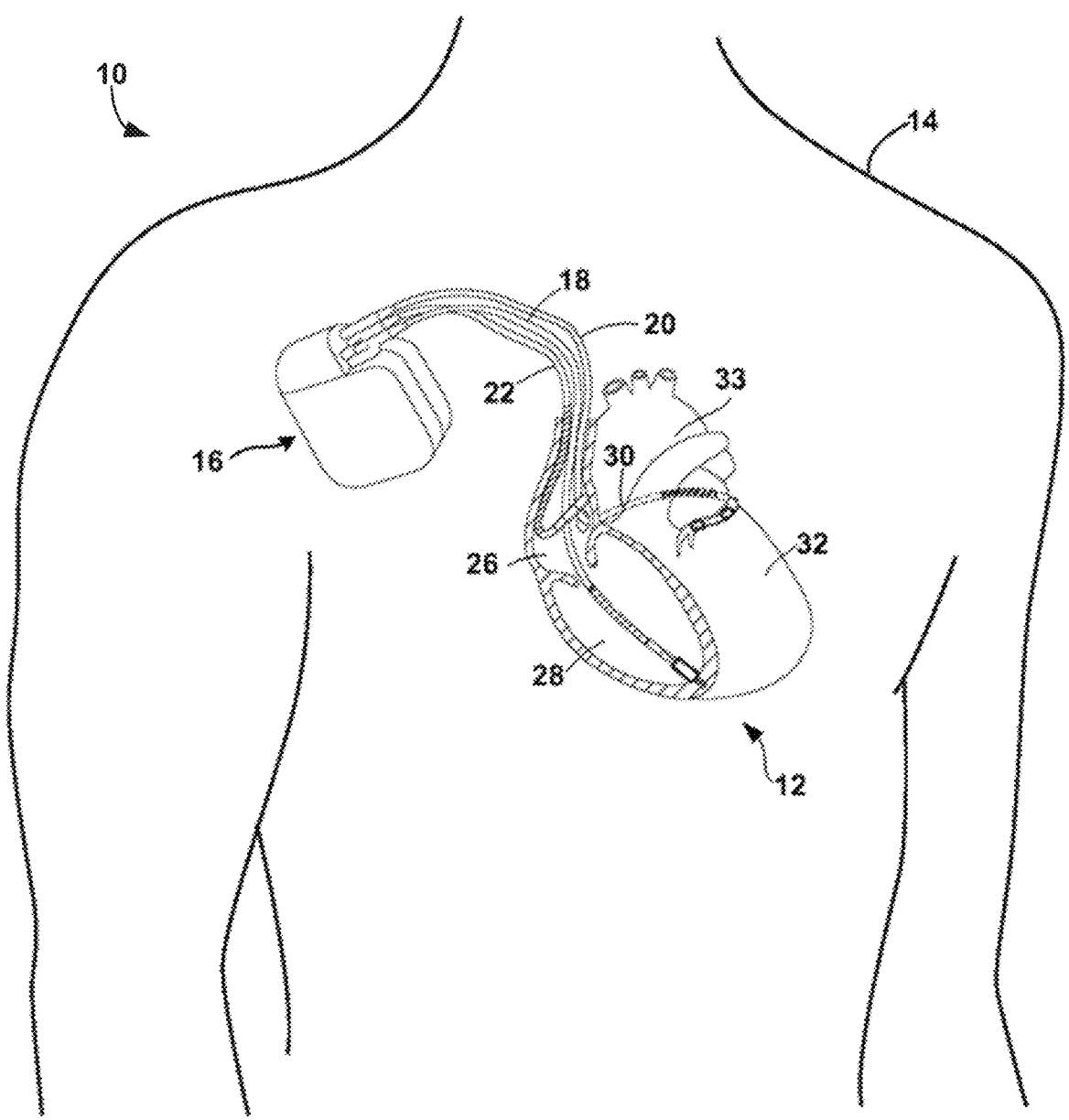
FIG. 11 is a diagram of an exemplary system including an exemplary implantable medical device (IMD).

FIG. 11 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals to and/or measures, or monitors electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 11, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., V-V delay, A-V delay and other various timings, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 12A:
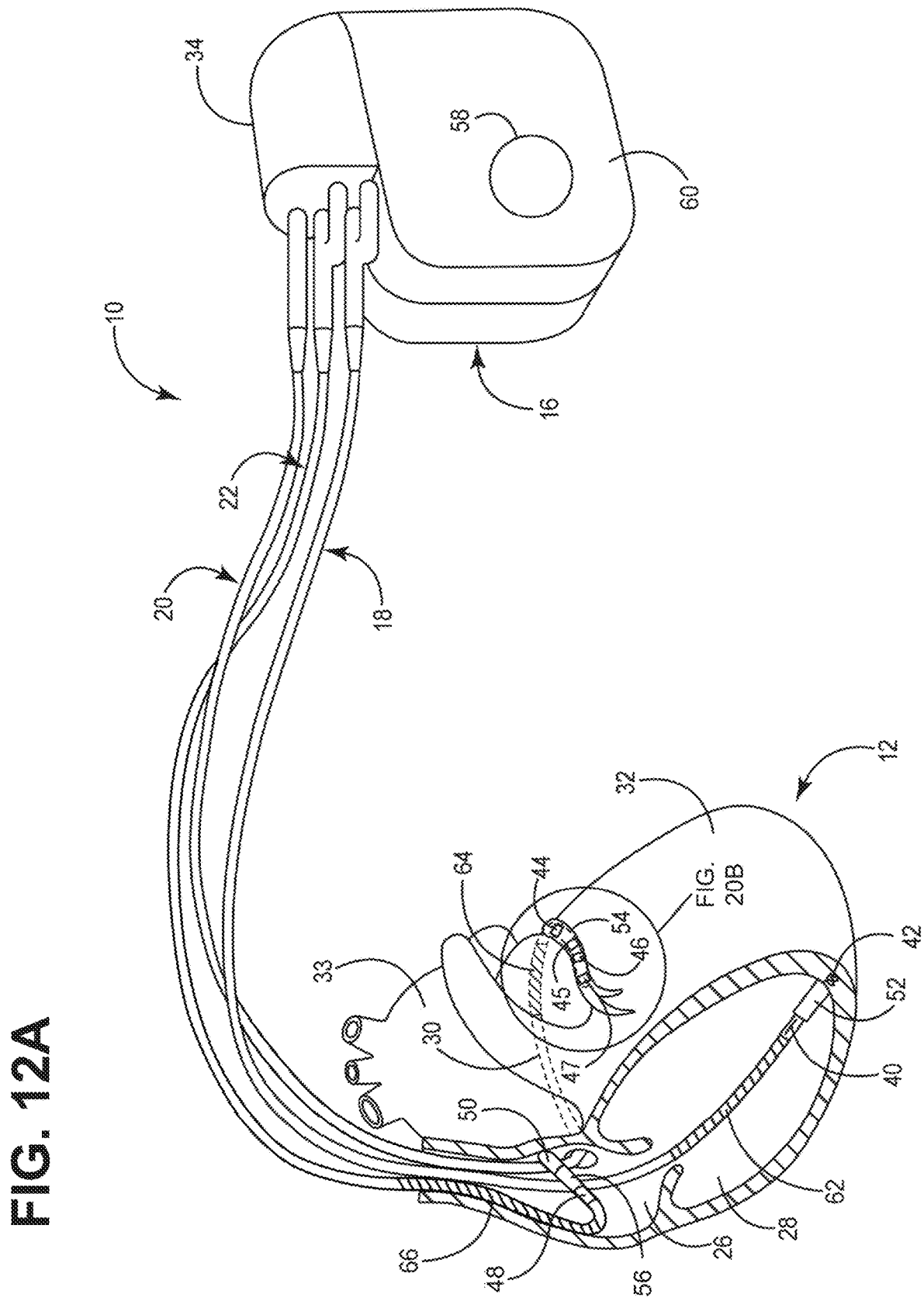
FIG. 12A is a diagram of the exemplary IMD of FIG. 11.
Figure 12B:
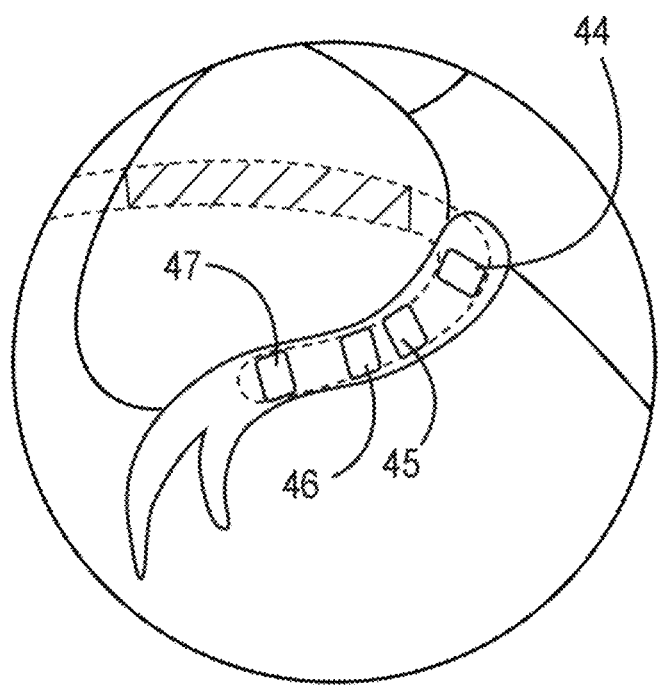
FIG. 12B is a diagram of an enlarged view of a distal end of the electrical lead disposed in the left ventricle of FIG. 12A.

FIGS. 12A-12B are conceptual diagrams illustrating the IMD 16 and the leads 18, 20, 22 of therapy system 10 of FIG. 11 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g., about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The sensed electrical signals may be used to adjust one or more pacing parameters such as, e.g., A-V interval, V-V interval, etc. to provide optimal and/or effective cardiac functionality. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 12A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. In other words, any of electrodes 40, 42, 44, 45, 46, 47, 48, 50, 58 may be used in combination to form a sensing vector, e.g., a sensing vector that may be used to evaluate and/or analyze the effectiveness of pacing therapy. It is to be understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy, may be used to sense electrical activity during pacing therapy.

As described in further detail with reference to FIG. 12A, the housing 60 may enclose a therapy delivery module that may include a stimulation generator for generating cardiac pacing pulses and defibrillation or cardioversion shocks, as well as a sensing module for monitoring electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity (e.g., for use in determining electrode effectiveness, for use in analyzing pacing therapy effectiveness, etc.) and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the exemplary therapy system 10 illustrated in FIGS. 11-13 is merely one example. In other examples, the therapy system may include epicardial leads and/or patch electrodes instead of or in addition to the transvenous leads 18, 20, 22 illustrated in FIG. 12A. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 11). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 11-13. Still further, other therapy systems may include a single lead that extends from the IMD 16 into the right atrium 26 or the right ventricle 28, or two leads that extend into a respective one of the right atrium 26 and the right ventricle 28.

Figure 13A:
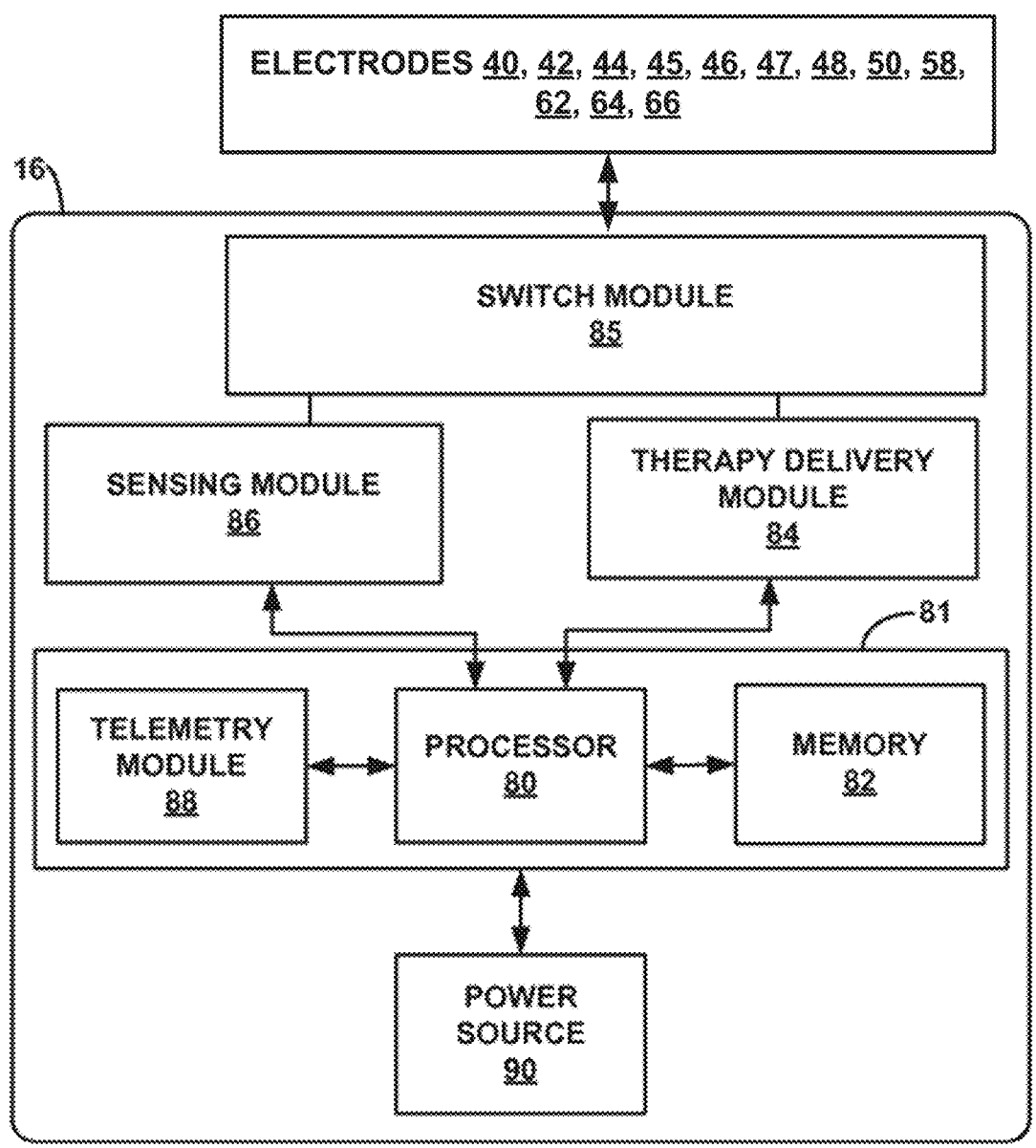
FIG. 13A is a block diagram of an exemplary IMD, e.g., the IMD of FIGS. 11-12.

FIG. 13A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., A-V delays, V-V delays, pacing pulses with the amplitudes, pulse widths, frequency, or electrode polarities, etc., which may be specified by one or more selected therapy programs (e.g., A-V and/or V-V delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy using a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals (e.g., intrinsic A-V conduction times, intrinsic V-V conduction times, etc.), which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 13B:
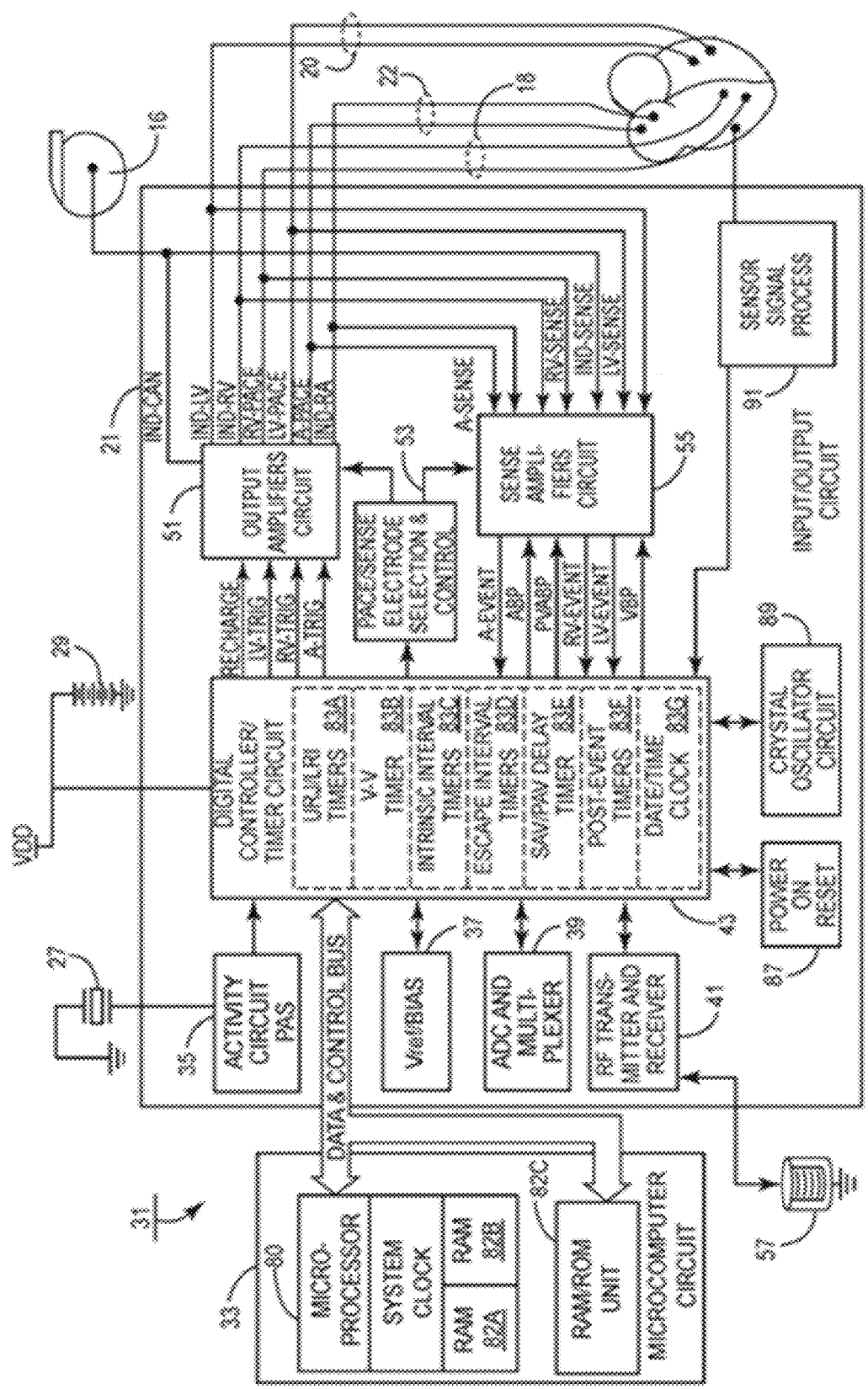
FIG. 13B is another block diagram of an exemplary IMD (e.g., an implantable pulse generator) circuitry and associated leads employed in the system of FIG. 11.

FIG. 13B is another embodiment of a functional block diagram for IMD 16. FIG. 13B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in exemplary implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer. The output signal of the patient activity sensor 27 may be processed and used as a RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the exemplary systems, apparatus, and methods described herein may be practiced in conjunction with alternate types of sensors such as oxygenation sensors, pressure sensors, pH sensors, and respiration sensors for use in providing rate responsive pacing capabilities. Alternately, QT time may be used as the rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative V-V delay intervals, A-V delay intervals, etc. and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 321 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an A-V delay interval timer 83E for timing the A-LVp delay (or A-RVp delay) from a preceding A-EVENT or A-TRIG, a post-ventricular timer 83F for timing post-ventricular time periods, and a date/time clock 83G.

The A-V delay interval timer 83E is loaded with an appropriate delay interval for one ventricular chamber (e.g., either an A-RVp delay or an A-LVp delay) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any A-V delay, and an atrial blanking period (ABP) during which atrial sensing is disabled. It should be noted that the starting of the post-atrial time periods and the A-V delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates A-V delays, V-V delays, post-ventricular time periods, and post-atrial time periods that vary with the sensor based escape interval established in response to the RCP(s) and/or with the intrinsic atrial rate and/or intrinsic ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV, and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

ILLUSTRATIVE EMBODIMENTS

Embodiment 1

A system for use in cardiac evaluation comprising:
electrode apparatus comprising a plurality of external electrodes to be located proximate a patient's skin; and computing apparatus comprising one or more processors, the computing apparatus coupled to the electrode apparatus and configured to:
- monitor electrical activity from the patient's skin using the plurality of external electrodes over a cardiac cycle,
- generate a surrogate cardiac electrical activation time based on the monitored electrical activity using baseline criterion,
- determine whether to correct the surrogate cardiac electrical activation time, and
- regenerate the surrogate cardiac electrical activation time based on the monitored electrical activity using correction criterion in response to a determination to correct the surrogate electrical activation time.

Embodiment 2

The system of embodiment 1, wherein monitoring electrical activity from the patient's skin using the plurality of external electrodes over a cardiac cycle comprises monitoring electrical activity from the patient's skin using the plurality of external electrodes over a cardiac depolarization cycle.

Embodiment 3

The system as in any one of embodiments 1-2, wherein the baseline criterion defines a start time point and an end time point for the surrogate cardiac electrical activation time, wherein the end time point corresponds to the time at which the maximum negative slope occurs within the electrical activity over the cardiac cycle.

Embodiment 4

The system as in any one of embodiments 1-3, wherein determining whether to correct the surrogate cardiac electrical activation time comprises determining to correct the surrogate cardiac electrical activation time with late correction if the surrogate cardiac electrical activation time is greater than or equal to a selected late correction threshold.

Embodiment 5

The system of embodiment 4, wherein the selected late correction threshold is a percentage of a QRS complex time extending from an onset of a QRS complex within the electrical activity over the cardiac cycle to an offset of the QRS complex, wherein the percentage is greater than or equal to 75%.

Embodiment 6

The system as in any one of embodiments 1-5, wherein determining whether to correct the surrogate cardiac electrical activation time comprises determining to correct the surrogate cardiac electrical activation time with early correction if the surrogate cardiac electrical activation time is less than or equal to a selected early correction threshold.

Embodiment 7

The system of embodiment 6, wherein the selected early correction threshold is a percentage of a QRS complex time extending from an onset of a QRS complex within the electrical activity over the cardiac cycle to an offset of the QRS complex, wherein the percentage is less than or equal to 25%.

Embodiment 8

The system as in any one of embodiments 1-7, wherein determining whether to correct the surrogate cardiac electrical activation time comprises determining to correct the surrogate cardiac electrical activation time with late correction if:
- right ventricular cardiac pacing or no cardiac pacing is being delivered to the patient;
- a minimum value of the electrical activity over the cardiac cycle occurs within a selected minimum time window of a QRS complex time extending from an onset of a QRS complex within the electrical activity over the cardiac cycle to an offset of the QRS complex, and
- a maximum value of the electrical activity over the cardiac cycle occurs within a selected maximum time window of the QRS complex time.

Embodiment 9

The system of embodiment 8, wherein the selected minimum time window extends between 15% and 50% of the QRS complex time, and the selected maximum time window extends between 50% and 85% of the QRS complex time.

Embodiment 10

The system as in any one of embodiments 8-9, wherein determining whether to correct the surrogate cardiac electrical activation time comprises determining to correct the surrogate cardiac electrical activation time with late correction further if:
- a magnitude of the maximum value of the electrical activity over the cardiac cycle relative a baseline value of the electrical activity is greater than a maximum threshold;
- a magnitude of the minimum value of the electrical activity over the cardiac cycle relative the baseline value of the electrical activity is greater than a minimum threshold; and
- a difference between the maximum value of the electrical activity and the minimum value of the electrical activity over the cardiac cycle is greater than a peak-to-peak threshold.

Embodiment 11

The system as in any one of embodiments 1-10, wherein determining whether to correct the surrogate cardiac electrical activation time comprises determining to correct the surrogate cardiac electrical activation time with early correction if:
- left ventricular cardiac pacing or biventricular cardiac pacing is being delivered to the patient;
- a difference between the maximum value of the electrical activity and the minimum value of the electrical activity over the cardiac cycle is less than a peak-to-peak threshold,
- a ratio of a magnitude of a minimum value of the electrical activity relative to a baseline value of the electrical activity over the cardiac cycle to a magnitude of a maximum value of the electrical activity relative to the baseline value of the electrical activity over the cardiac cycle is greater than a ratio threshold;

the magnitude of the maximum value of the electrical activity relative to the baseline value over the cardiac cycle is less than a maximum threshold; and the minimum value occurs before the maximum value within the electrical activity over the cardiac cycle.

Embodiment 12

The system of embodiment 11, wherein determining whether to correct the surrogate cardiac electrical activation time comprises determining to correct the surrogate cardiac electrical activation time with early correction further if:

the minimum value does not occur within a selected onset time window of a QRS complex time extending from an onset of a QRS complex within the electrical activity over the cardiac cycle; and the maximum value does not occur within a selected offset time window of the QRS complex time extending to an offset of the QRS complex.

Embodiment 13

The system as in any one of embodiments 1-12, wherein determining whether to correct the surrogate cardiac electrical activation time comprises determining to correct the surrogate cardiac electrical activation time with correlation correction if:

the morphology of the electrical activity over the cardiac cycle monitored by a selected electrode is similar to the morphology of electrical activity over the cardiac cycle monitored by one or more electrodes located proximate to the selected electrode; and the surrogate cardiac electrical activation time generated from the electrical activity over the cardiac cycle monitored by a selected electrode is outside of a selected range from the median of the surrogate cardiac electrical activation times generated from the electrical activity monitored by the one or more electrodes located proximate to the selected electrode.

Embodiment 14

The system of embodiment 13, wherein the correction criterion defines a start time point and an end time point for the surrogate cardiac electrical activation time, wherein the end time point corresponds to a median end time point of the surrogate cardiac electrical activation times generated from the electrical activity monitored by the one or more electrodes located proximate to the selected electrode when regenerating the surrogate cardiac electrical activation time using correlation correction.

Embodiment 15

The system as in any one of embodiments 1-14, wherein the correction criterion defines a start time point and an end time point for the surrogate cardiac electrical activation time, wherein the end time point is set to when the electrical activity is less than half of a maximum value of the electrical activity after occurrence of the maximum value of the electrical activity when regenerating the surrogate cardiac electrical activation time using late correction.

Embodiment 16

The system as in any one of embodiments 1-15, wherein the correction criterion defines a start time point and an end time point for the surrogate cardiac electrical activation time, wherein the end time point is set to when the electrical activity is less than half of a minimum value of the electrical activity before occurrence of the minimum value of the electrical activity when regenerating the surrogate cardiac electrical activation time using early correction.

Embodiment 17

A method for use in cardiac evaluation comprising:
monitoring electrical activity from a patient's skin using a plurality of electrodes to generate over a cardiac cycle;
generating a surrogate cardiac electrical activation time based on the monitored electrical activity using baseline criterion;
determining whether to correct the surrogate cardiac electrical activation time; and
regenerating the surrogate cardiac electrical activation time based on the monitored electrical activity using correction criterion in response to a determination to correct the surrogate electrical activation time.

Embodiment 18

The method of embodiment 17, wherein monitoring electrical activity from the patient's skin using the plurality of external electrodes over a cardiac cycle comprises monitoring electrical activity from the patient's skin using the plurality of external electrodes over a cardiac depolarization cycle.

Embodiment 19

The method as in any one of embodiments 17-18, wherein the baseline criterion defines a start time point and an end time point for the surrogate cardiac electrical activation time, wherein the end time point corresponds to the time at which the maximum negative slope occurs within the electrical activity over the cardiac cycle.

Embodiment 20

The method as in any one of embodiments 17-19, wherein determining whether to correct the surrogate cardiac electrical activation time comprises determining to correct the surrogate cardiac electrical activation time with late correction if the surrogate cardiac electrical activation time is greater than or equal to a selected late correction threshold.

Embodiment 21

The method of embodiment 20, wherein the selected late correction threshold is a percentage of a QRS complex time extending from an onset of a QRS complex within the electrical activity over the cardiac cycle to an offset of the QRS complex, wherein the percentage is greater than or equal to 75%.

Embodiment 22

The method as in any one of embodiments 17-21, wherein determining whether to correct the surrogate cardiac electrical activation time comprises determining to correct the surrogate cardiac electrical activation time with early correction if the surrogate cardiac electrical activation time is less than or equal to a selected early correction threshold.

Embodiment 23

The method of embodiment 22, wherein the selected early correction threshold is a percentage of a QRS complex time extending from an onset of a QRS complex within the electrical activity over the cardiac cycle to an offset of the QRS complex, wherein the percentage is less than or equal to 25%.

Embodiment 24

The method as in any one of embodiments 17-23, wherein determining whether to correct the surrogate cardiac electrical activation time comprises determining to correct the surrogate cardiac electrical activation time with late correction if:
right ventricular cardiac pacing or no cardiac pacing is being delivered to the patient;
a minimum value of the electrical activity over the cardiac cycle occurs within a selected minimum time window of a QRS complex time extending from an onset of a QRS complex within the electrical activity over the cardiac cycle to an offset of the QRS complex, and
a maximum value of the electrical activity over the cardiac cycle occurs within a selected maximum time window of the QRS complex time.

Embodiment 25

The method of embodiment 24, wherein the selected minimum time window extends between 15% and 50% of the QRS complex time, and the selected maximum time window extends between 50% and 85% of the QRS complex time.

Embodiment 26

The method as in any one of embodiments 24-25, wherein determining whether to correct the surrogate cardiac electrical activation time comprises determining to correct the surrogate cardiac electrical activation time with late correction further if:
a magnitude of the maximum value of the electrical activity over the cardiac cycle relative a baseline value of the electrical activity is greater than a maximum threshold;
a magnitude of the minimum value of the electrical activity over the cardiac cycle relative the baseline value of the electrical activity is greater than a minimum threshold; and
a difference between the maximum value of the electrical activity and the minimum value of the electrical activity over the cardiac cycle is greater than a peak-to-peak threshold.

Embodiment 27

The method as in any one of embodiments 17-26, wherein determining whether to correct the surrogate cardiac electrical activation time comprises determining to correct the surrogate cardiac electrical activation time with early correction if:
left ventricular cardiac pacing or biventricular cardiac pacing is being delivered to the patient;
a difference between the maximum value of the electrical activity and the minimum value of the electrical activity over the cardiac cycle is less than a peak-to-peak threshold,
a ratio of a magnitude of a minimum value of the electrical activity relative to a baseline value of the electrical activity over the cardiac cycle to a magnitude of a maximum value of the electrical activity relative to the baseline value of the electrical activity over the cardiac cycle is greater than a ratio threshold;
the magnitude of the maximum value of the electrical activity relative to the baseline value over the cardiac cycle is less than a maximum threshold; and
the minimum value occurs before the maximum value within the electrical activity over the cardiac cycle.

Embodiment 28

The method of embodiment 27, wherein determining whether to correct the surrogate cardiac electrical activation time comprises determining to correct the surrogate cardiac electrical activation time with early correction further if:
the minimum value does not occur within a selected onset time window of a QRS complex time extending from an onset of a QRS complex within the electrical activity over the cardiac cycle; and
the maximum value does not occur within a selected offset time window of the QRS complex time extending to an offset of the QRS complex.

Embodiment 29

The method as in any one of embodiments 17-28, wherein determining whether to correct the surrogate cardiac electrical activation time comprises determining to correct the surrogate cardiac electrical activation time with correlation correction if:
the morphology of the electrical activity over the cardiac cycle monitored by a selected electrode is similar to the morphology of electrical activity over the cardiac cycle monitored by one or more electrodes located proximate to the selected electrode; and
the surrogate cardiac electrical activation time generated from the electrical activity over the cardiac cycle monitored by a selected electrode is outside of a selected range from the median of the surrogate cardiac electrical activation times generated from the electrical activity monitored by the one or more electrodes located proximate to the selected electrode.

Embodiment 30

The method of embodiment 29, wherein the correction criterion defines a start time point and an end time point for the surrogate cardiac electrical activation time, wherein the end time point corresponds to a median end time point of the surrogate cardiac electrical activation times generated from the electrical activity monitored by the one or more electrodes located proximate to the selected electrode when regenerating the surrogate cardiac electrical activation time using correlation correction.

Embodiment 31

The method as in any one of embodiments 17-30, wherein the correction criterion defines a start time point and an end time point for the surrogate cardiac electrical activation time, wherein the end time point is set to when the electrical activity is less than half of a maximum value of the electrical activity after occurrence of the maximum value of the electrical activity when regenerating the surrogate cardiac electrical activation time using late correction.

Embodiment 32

The method as in any one of embodiments 17-31, wherein the correction criterion defines a start time point and an end time point for the surrogate cardiac electrical activation time, wherein the end time point is set to when the electrical activity is less than half of a minimum value of the electrical activity before occurrence of the minimum value of the electrical activity when regenerating the surrogate cardiac electrical activation time using early correction.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for use in cardiac evaluation comprising:
   electrode apparatus comprising a plurality of external electrodes to be located proximate a patient's skin; and
   computing apparatus comprising one or more processors, the computing apparatus coupled to the electrode apparatus and configured to:
   monitor electrical activity from the patient's skin using the plurality of external electrodes over a cardiac cycle,
   generate a surrogate cardiac electrical activation time based on the monitored electrical activity using baseline criterion,
   determine whether to correct the surrogate cardiac electrical activation time, wherein determining whether to correct the surrogate cardiac electrical activation time comprises determining to correct the surrogate cardiac electrical activation time with late correction if the surrogate cardiac electrical activation time is greater than or equal to a selected late correction threshold, and
   regenerate the surrogate cardiac electrical activation time based on the monitored electrical activity using correction criterion in response to a determination to correct the surrogate electrical activation time, wherein the correction criterion comprises at least one of early correction criterion and late correction criterion, wherein regenerating the surrogate cardiac electrical activation time based on the monitored electrical activity using correction criterion in response to a determination to correct the surrogate electrical activation time comprises regenerating the surrogate cardiac electrical activation time based on the monitored electrical activity using the late correction criterion in response to determination to correct the surrogate cardiac electrical activation time with late correction.

2. The system of claim 1, wherein monitoring electrical activity from the patient's skin using the plurality of external electrodes over a cardiac cycle comprises monitoring electrical activity from the patient's skin using the plurality of external electrodes over a cardiac depolarization cycle.

3. The system of claim 1, wherein the baseline criterion defines a start time point and an end time point for the surrogate cardiac electrical activation time, wherein the end time point corresponds to the time at which the maximum negative slope occurs within the electrical activity over the cardiac cycle.

4. The system of claim 1, wherein the selected late correction threshold is a percentage of a QRS complex time extending from an onset of a QRS complex within the electrical activity over the cardiac cycle to an offset of the QRS complex, wherein the percentage is greater than or equal to 75%.

5. The system of claim 1, wherein determining whether to correct the surrogate cardiac electrical activation time further comprises determining to correct the surrogate cardiac electrical activation time with early correction if the surrogate cardiac electrical activation time is less than or equal to a selected early correction threshold,
   wherein regenerating the surrogate cardiac electrical activation time based on the monitored electrical activity using correction criterion in response to a determination to correct the surrogate electrical activation time further comprises regenerating the surrogate cardiac electrical activation time based on the monitored electrical activity using the early correction criterion in response to determination to correct the surrogate cardiac electrical activation time with early correction.

6. The system of claim 5, wherein the selected early correction threshold is a percentage of a QRS complex time extending from an onset of a QRS complex within the electrical activity over the cardiac cycle to an offset of the QRS complex, wherein the percentage is less than or equal to 25%.

7. The system of claim 1, wherein determining whether to correct the surrogate cardiac electrical activation time further comprises determining to correct the surrogate cardiac electrical activation time with late correction if:
   right ventricular cardiac pacing or no cardiac pacing is being delivered to the patient;
   a minimum value of the electrical activity over the cardiac cycle occurs within a selected minimum time window of a QRS complex time extending from an onset of a QRS complex within the electrical activity over the cardiac cycle to an offset of the QRS complex; and
   a maximum value of the electrical activity over the cardiac cycle occurs within a selected maximum time window of the QRS complex time.

8. The system of claim 7, wherein the selected minimum time window extends between 15% and 50% of the QRS complex time, and the selected maximum time window extends between 50% and 85% of the QRS complex time.

9. The system of claim 7, wherein determining whether to correct the surrogate cardiac electrical activation time further comprises determining to correct the surrogate cardiac electrical activation time with late correction further if:
   a magnitude of the maximum value of the electrical activity over the cardiac cycle relative a baseline value of the electrical activity is greater than a maximum threshold;
   a magnitude of the minimum value of the electrical activity over the cardiac cycle relative the baseline value of the electrical activity is greater than a minimum threshold; and
   a difference between the maximum value of the electrical activity and the minimum value of the electrical activity over the cardiac cycle is greater than a peak-to-peak threshold.

10. The system of claim 1, wherein determining whether to correct the surrogate cardiac electrical activation time further comprises determining to correct the surrogate cardiac electrical activation time with early correction if:
  left ventricular cardiac pacing or biventricular cardiac pacing is being delivered to the patient;
  a difference between a maximum value of the electrical activity and a minimum value of the electrical activity over the cardiac cycle is less than a peak-to-peak threshold,
  a ratio of a magnitude of the minimum value of the electrical activity relative to a baseline value of the electrical activity over the cardiac cycle to a magnitude of the maximum value of the electrical activity relative to the baseline value of the electrical activity over the cardiac cycle is greater than a ratio threshold;
  the magnitude of the maximum value of the electrical activity relative to the baseline value over the cardiac cycle is less than a maximum threshold; and
  the minimum value occurs before the maximum value within the electrical activity over the cardiac cycle,
  wherein regenerating the surrogate cardiac electrical activation time based on the monitored electrical activity using correction criterion in response to a determination to correct the surrogate electrical activation time further comprises regenerating the surrogate cardiac electrical activation time based on the monitored electrical activity using the early correction criterion in response to determination to correct the surrogate cardiac electrical activation time with early correction.

11. The system of claim 10, wherein determining whether to correct the surrogate cardiac electrical activation time further comprises determining to correct the surrogate cardiac electrical activation time with early correction further if:
  the minimum value does not occur within a selected onset time window of a QRS complex time extending from an onset of a QRS complex within the electrical activity over the cardiac cycle; and
  the maximum value does not occur within a selected offset time window of the QRS complex time extending to an offset of the QRS complex.

12. The system of claim 1, wherein the correction criterion further comprises correlation criterion, wherein determining whether to correct the surrogate cardiac electrical activation time further comprises determining to correct the surrogate cardiac electrical activation time with correlation correction if:
  a morphology of the electrical activity over the cardiac cycle monitored by a selected electrode is similar to the morphology of electrical activity over the cardiac cycle monitored by one or more electrodes located proximate to the selected electrode; and
  the surrogate cardiac electrical activation time generated from the electrical activity over the cardiac cycle monitored by the selected electrode is outside of a selected range from a median of the surrogate cardiac electrical activation times generated from the electrical activity monitored by the one or more electrodes located proximate to the selected electrode,
  wherein regenerating the surrogate cardiac electrical activation time based on the monitored electrical activity using correction criterion in response to a determination to correct the surrogate electrical activation time further comprises regenerating the surrogate cardiac electrical activation time based on the monitored electrical activity using the correlation correction criterion in response to determination to correct the surrogate cardiac electrical activation time with correlation correction.

13. The system of claim 12, wherein the correlation correction criterion defines a start time point and an end time point for the surrogate cardiac electrical activation time, wherein the end time point corresponds to a median end time point of the surrogate cardiac electrical activation times generated from the electrical activity monitored by the one or more electrodes located proximate to the selected electrode when regenerating the surrogate cardiac electrical activation time using correlation correction.

14. The system of claim 1, wherein the late correction criterion defines a start time point and an end time point for the surrogate cardiac electrical activation time, wherein the end time point is set to when the electrical activity is less than half of a maximum value of the electrical activity after occurrence of the maximum value of the electrical activity when regenerating the surrogate cardiac electrical activation time using late correction.

15. The system of claim 1, wherein the early correction criterion defines a start time point and an end time point for the surrogate cardiac electrical activation time, wherein the end time point is set to when the electrical activity is less than half of a minimum value of the electrical activity before occurrence of the minimum value of the electrical activity when regenerating the surrogate cardiac electrical activation time using early correction.

16. A method for use in cardiac evaluation comprising:
  monitoring electrical activity from a patient's skin using a plurality of external electrodes to generate over a cardiac cycle;
  generating a surrogate cardiac electrical activation time based on the monitored electrical activity using baseline criterion;
  determining whether to correct the surrogate cardiac electrical activation time, wherein determining whether to correct the surrogate cardiac electrical activation time comprises determining to correct the surrogate cardiac electrical activation time with late correction if the surrogate cardiac electrical activation time is greater than or equal to a selected late correction threshold; and
  regenerating the surrogate cardiac electrical activation time based on the monitored electrical activity using correction criterion in response to a determination to correct the surrogate electrical activation time, wherein the correction criterion comprises at least one of early correction criterion and late correction criterion, wherein regenerating the surrogate cardiac electrical activation time based on the monitored electrical activity using correction criterion in response to a determination to correct the surrogate electrical activation time comprises regenerating the surrogate cardiac electrical activation time based on the monitored electrical activity using the late correction criterion in response to determination to correct the surrogate cardiac electrical activation time with late correction.

17. The method of claim 16, wherein monitoring electrical activity from the patient's skin using the plurality of external electrodes over a cardiac cycle comprises monitoring electrical activity from the patient's skin using the plurality of external electrodes over a cardiac depolarization cycle.

18. The method of claim 16, wherein the baseline criterion defines a start time point and an end time point for the surrogate cardiac electrical activation time, wherein the end time point corresponds to the time at which the maximum negative slope occurs within the electrical activity over the cardiac cycle.

19. The method of claim 16, wherein the selected late correction threshold is a percentage of a QRS complex time extending from an onset of a QRS complex within the electrical activity over the cardiac cycle to an offset of the QRS complex, wherein the percentage is greater than or equal to 75%.

20. The method of claim 16, wherein determining whether to correct the surrogate cardiac electrical activation time further comprises determining to correct the surrogate cardiac electrical activation time with early correction if the surrogate cardiac electrical activation time is less than or equal to a selected early correction threshold,
wherein regenerating the surrogate cardiac electrical activation time based on the monitored electrical activity using correction criterion in response to a determination to correct the surrogate electrical activation time further comprises regenerating the surrogate cardiac electrical activation time based on the monitored electrical activity using the early correction criterion in response to determination to correct the surrogate cardiac electrical activation time with early correction.

21. The method of claim 20, wherein the selected early correction threshold is a percentage of a QRS complex time extending from an onset of a QRS complex within the electrical activity over the cardiac cycle to an offset of the QRS complex, wherein the percentage is less than or equal to 25%.

22. The method of claim 16, wherein determining whether to correct the surrogate cardiac electrical activation time further comprises determining to correct the surrogate cardiac electrical activation time with late correction if:
right ventricular cardiac pacing or no cardiac pacing is being delivered to the patient;
a minimum value of the electrical activity over the cardiac cycle occurs within a selected minimum time window of a QRS complex time extending from an onset of a QRS complex within the electrical activity over the cardiac cycle to an offset of the QRS complex; and
a maximum value of the electrical activity over the cardiac cycle occurs within a selected maximum time window of the QRS complex time.

23. The method of claim 22, wherein the selected minimum time window extends between 15% and 50% of the QRS complex time, and the selected maximum time window extends between 50% and 85% of the QRS complex time.

24. The method of claim 22, wherein determining whether to correct the surrogate cardiac electrical activation time further comprises determining to correct the surrogate cardiac electrical activation time with late correction further if:
a magnitude of the maximum value of the electrical activity over the cardiac cycle relative a baseline value of the electrical activity is greater than a maximum threshold;
a magnitude of the minimum value of the electrical activity over the cardiac cycle relative the baseline value of the electrical activity is greater than a minimum threshold; and
a difference between the maximum value of the electrical activity and the minimum value of the electrical activity over the cardiac cycle is greater than a peak-to-peak threshold.

25. The method of claim 16, wherein determining whether to correct the surrogate cardiac electrical activation time further comprises determining to correct the surrogate cardiac electrical activation time with early correction if:
left ventricular cardiac pacing or biventricular cardiac pacing is being delivered to the patient;
a difference between a maximum value of the electrical activity and a minimum value of the electrical activity over the cardiac cycle is less than a peak-to-peak threshold,
a ratio of a magnitude of the minimum value of the electrical activity relative to a baseline value of the electrical activity over the cardiac cycle to a magnitude of the maximum value of the electrical activity relative to the baseline value of the electrical activity over the cardiac cycle is greater than a ratio threshold;
the magnitude of the maximum value of the electrical activity relative to the baseline value over the cardiac cycle is less than a maximum threshold; and
the minimum value occurs before the maximum value within the electrical activity over the cardiac cycle,
wherein regenerating the surrogate cardiac electrical activation time based on the monitored electrical activity using correction criterion in response to a determination to correct the surrogate electrical activation time further comprises regenerating the surrogate cardiac electrical activation time based on the monitored electrical activity using the early correction criterion in response to determination to correct the surrogate cardiac electrical activation time with early correction.

26. The method of claim 25, wherein determining whether to correct the surrogate cardiac electrical activation time further comprises determining to correct the surrogate cardiac electrical activation time with early correction further if:
the minimum value does not occur within a selected onset time window of a QRS complex time extending from an onset of a QRS complex within the electrical activity over the cardiac cycle; and
the maximum value does not occur within a selected offset time window of the QRS complex time extending to an offset of the QRS complex.

27. The method of claim 16, wherein the correction criterion further comprises correlation criterion, wherein determining whether to correct the surrogate cardiac electrical activation time comprises determining to correct the surrogate cardiac electrical activation time with correlation correction if:
a morphology of the electrical activity over the cardiac cycle monitored by a selected electrode is similar to the morphology of electrical activity over the cardiac cycle monitored by one or more electrodes located proximate to the selected electrode; and
the surrogate cardiac electrical activation time generated from the electrical activity over the cardiac cycle monitored by the selected electrode is outside of a selected range from a median of the surrogate cardiac electrical activation times generated from the electrical activity monitored by the one or more electrodes located proximate to the selected electrode,
wherein regenerating the surrogate cardiac electrical activation time based on the monitored electrical activity using correction criterion in response to a determination to correct the surrogate electrical activation time comprises regenerating the surrogate cardiac electrical activation time based on the monitored electrical activity using the correlation correction criterion in response to determination to correct the surrogate cardiac electrical activation time with correlation correction.

28. The method of claim 27, wherein the correlation correction criterion defines a start time point and an end time point for the surrogate cardiac electrical activation time, wherein the end time point corresponds to a median end time point of the surrogate cardiac electrical activation times generated from the electrical activity monitored by the one or more electrodes located proximate to the selected electrode when regenerating the surrogate cardiac electrical activation time using correlation correction.

29. The method of claim 16, wherein the late correction criterion defines a start time point and an end time point for the surrogate cardiac electrical activation time, wherein the end time point is set to when the electrical activity is less than half of a maximum value of the electrical activity after occurrence of the maximum value of the electrical activity when regenerating the surrogate cardiac electrical activation time using late correction.

30. The method of claim 16, wherein the early correction criterion defines a start time point and an end time point for the surrogate cardiac electrical activation time, wherein the end time point is set to when the electrical activity is less than half of a minimum value of the electrical activity before occurrence of the minimum value of the electrical activity when regenerating the surrogate cardiac electrical activation time using early correction.

31. A system for use in cardiac evaluation comprising:
electrode apparatus comprising a plurality of external electrodes to be located proximate a patient's skin; and
computing apparatus comprising one or more processors, the computing apparatus coupled to the electrode apparatus and configured to:
monitor electrical activity from the patient's skin using the plurality of external electrodes over a cardiac cycle,
generate a surrogate cardiac electrical activation time based on the monitored electrical activity using baseline criterion,
determine whether to correct the surrogate cardiac electrical activation time, wherein determining whether to correct the surrogate cardiac electrical activation time comprises determining to correct the surrogate cardiac electrical activation time with early correction if the surrogate cardiac electrical activation time is less than or equal to a selected early correction threshold, and
regenerate the surrogate cardiac electrical activation time based on the monitored electrical activity using correction criterion in response to a determination to correct the surrogate electrical activation time, wherein the correction criterion comprises at least one of early correction criterion and late correction criterion, wherein regenerating the surrogate cardiac electrical activation time based on the monitored electrical activity using correction criterion in response to a determination to correct the surrogate electrical activation time comprises regenerating the surrogate cardiac electrical activation time based on the monitored electrical activity using the early correction criterion in response to determination to correct the surrogate cardiac electrical activation time with early correction.

32. The system of claim 31, wherein monitoring electrical activity from the patient's skin using the plurality of external electrodes over a cardiac cycle comprises monitoring electrical activity from the patient's skin using the plurality of external electrodes over a cardiac depolarization cycle.

33. The system of claim 31, wherein the baseline criterion defines a start time point and an end time point for the surrogate cardiac electrical activation time, wherein the end time point corresponds to the time at which the maximum negative slope occurs within the electrical activity over the cardiac cycle.

34. The system of claim 31, wherein the selected early correction threshold is a percentage of a QRS complex time extending from an onset of a QRS complex within the electrical activity over the cardiac cycle to an offset of the QRS complex, wherein the percentage is less than or equal to 25%.

35. The system of claim 31, wherein determining whether to correct the surrogate cardiac electrical activation time further comprises determining to correct the surrogate cardiac electrical activation time with late correction if:
right ventricular cardiac pacing or no cardiac pacing is being delivered to the patient;
a minimum value of the electrical activity over the cardiac cycle occurs within a selected minimum time window of a QRS complex time extending from an onset of a QRS complex within the electrical activity over the cardiac cycle to an offset of the QRS complex, and
a maximum value of the electrical activity over the cardiac cycle occurs within a selected maximum time window of the QRS complex time,
wherein regenerating the surrogate cardiac electrical activation time based on the monitored electrical activity using correction criterion in response to a determination to correct the surrogate electrical activation time further comprises regenerating the surrogate cardiac electrical activation time based on the monitored electrical activity using the late correction criterion in response to determination to correct the surrogate cardiac electrical activation time with late correction.

36. The system of claim 31, wherein determining whether to correct the surrogate cardiac electrical activation time further comprises determining to correct the surrogate cardiac electrical activation time with early correction if:
left ventricular cardiac pacing or biventricular cardiac pacing is being delivered to the patient;
a difference between a maximum value of the electrical activity and a minimum value of the electrical activity over the cardiac cycle is less than a peak-to-peak threshold,
a ratio of a magnitude of the minimum value of the electrical activity relative to a baseline value of the electrical activity over the cardiac cycle to a magnitude of the maximum value of the electrical activity relative to the baseline value of the electrical activity over the cardiac cycle is greater than a ratio threshold;
the magnitude of the maximum value of the electrical activity relative to the baseline value over the cardiac cycle is less than a maximum threshold; and
the minimum value occurs before the maximum value within the electrical activity over the cardiac cycle.

37. The system of claim 31, wherein the correction criterion further comprises correlation criterion, wherein determining whether to correct the surrogate cardiac electrical activation time further comprises determining to correct the surrogate cardiac electrical activation time with correlation correction if:
a morphology of the electrical activity over the cardiac cycle monitored by a selected electrode is similar to the morphology of electrical activity over the cardiac cycle monitored by one or more electrodes located proximate to the selected electrode; and the surrogate cardiac electrical activation time generated from the electrical activity over the cardiac cycle monitored by the selected electrode is outside of a selected range from a median of the surrogate cardiac electrical activation times generated from the electrical activity monitored by the one or more electrodes located proximate to the selected electrode, wherein regenerating the surrogate cardiac electrical activation time based on the monitored electrical activity using correction criterion in response to a determination to correct the surrogate electrical activation time comprises regenerating the surrogate cardiac electrical activation time based on the monitored electrical activity using the correlation correction criterion in response to determination to correct the surrogate cardiac electrical activation time with correlation correction.

38. The system of claim 37, wherein the correlation correction criterion defines a start time point and an end time point for the surrogate cardiac electrical activation time, wherein the end time point corresponds to a median end time point of the surrogate cardiac electrical activation times generated from the electrical activity monitored by the one or more electrodes located proximate to the selected electrode when regenerating the surrogate cardiac electrical activation time using correlation correction.

39. The system of claim 31, wherein the late correction criterion defines a start time point and an end time point for the surrogate cardiac electrical activation time, wherein the end time point is set to when the electrical activity is less than half of a maximum value of the electrical activity after occurrence of the maximum value of the electrical activity when regenerating the surrogate cardiac electrical activation time using late correction.

40. The system of claim 31, wherein the early correction criterion defines a start time point and an end time point for the surrogate cardiac electrical activation time, wherein the end time point is set to when the electrical activity is less than half of a minimum value of the electrical activity before occurrence of the minimum value of the electrical activity when regenerating the surrogate cardiac electrical activation time using early correction.

41. A method for use in cardiac evaluation comprising:
monitoring electrical activity from a patient's skin using a plurality of external electrodes to generate over a cardiac cycle;
generating a surrogate cardiac electrical activation time based on the monitored electrical activity using baseline criterion;
determining whether to correct the surrogate cardiac electrical activation time, wherein determining whether to correct the surrogate cardiac electrical activation time comprises determining to correct the surrogate cardiac electrical activation time with early correction if the surrogate cardiac electrical activation time is less than or equal to a selected early correction threshold; and
regenerating the surrogate cardiac electrical activation time based on the monitored electrical activity using correction criterion in response to a determination to correct the surrogate electrical activation time, wherein the correction criterion comprises at least one of early correction criterion and late correction criterion, wherein regenerating the surrogate cardiac electrical activation time based on the monitored electrical activity using correction criterion in response to a determination to correct the surrogate electrical activation time comprises regenerating the surrogate cardiac electrical activation time based on the monitored electrical activity using the early correction criterion in response to determination to correct the surrogate cardiac electrical activation time with early correction.

42. The method of claim 41, wherein monitoring electrical activity from the patient's skin using the plurality of external electrodes over a cardiac cycle comprises monitoring electrical activity from the patient's skin using the plurality of external electrodes over a cardiac depolarization cycle.

43. The method of claim 41, wherein the baseline criterion defines a start time point and an end time point for the surrogate cardiac electrical activation time, wherein the end time point corresponds to the time at which the maximum negative slope occurs within the electrical activity over the cardiac cycle.

44. The method of claim 41, wherein the selected early correction threshold is a percentage of a QRS complex time extending from an onset of a QRS complex within the electrical activity over the cardiac cycle to an offset of the QRS complex, wherein the percentage is less than or equal to 25%.

45. The method of claim 41, wherein determining whether to correct the surrogate cardiac electrical activation time further comprises determining to correct the surrogate cardiac electrical activation time with late correction if:
right ventricular cardiac pacing or no cardiac pacing is being delivered to the patient;
a minimum value of the electrical activity over the cardiac cycle occurs within a selected minimum time window of a QRS complex time extending from an onset of a QRS complex within the electrical activity over the cardiac cycle to an offset of the QRS complex, and
a maximum value of the electrical activity over the cardiac cycle occurs within a selected maximum time window of the QRS complex time,
wherein regenerating the surrogate cardiac electrical activation time based on the monitored electrical activity using correction criterion in response to a determination to correct the surrogate electrical activation time comprises regenerating the surrogate cardiac electrical activation time based on the monitored electrical activity using the late correction criterion in response to determination to correct the surrogate cardiac electrical activation time with late correction.

46. The method of claim 41, wherein determining whether to correct the surrogate cardiac electrical activation time further comprises determining to correct the surrogate cardiac electrical activation time with early correction if:
left ventricular cardiac pacing or biventricular cardiac pacing is being delivered to the patient;
a difference between a maximum value of the electrical activity and a minimum value of the electrical activity over the cardiac cycle is less than a peak-to-peak threshold,
a ratio of a magnitude of the minimum value of the electrical activity relative to a baseline value of the electrical activity over the cardiac cycle to a magnitude of the maximum value of the electrical activity relative to the baseline value of the electrical activity over the cardiac cycle is greater than a ratio threshold;
the magnitude of the maximum value of the electrical activity relative to the baseline value over the cardiac cycle is less than a maximum threshold; and
the minimum value occurs before the maximum value within the electrical activity over the cardiac cycle, wherein regenerating the surrogate cardiac electrical activation time based on the monitored electrical activity using correction criterion in response to a determination to correct the surrogate electrical activation time comprises regenerating the surrogate cardiac electrical activation time based on the monitored electrical activity using the early correction criterion in response to determination to correct the surrogate cardiac electrical activation time with early correction.

47. The method of claim 41, wherein the correction criterion further comprises correlation criterion, wherein determining whether to correct the surrogate cardiac electrical activation time further comprises determining to correct the surrogate cardiac electrical activation time with correlation correction if:
  a morphology of the electrical activity over the cardiac cycle monitored by a selected electrode is similar to the morphology of electrical activity over the cardiac cycle monitored by one or more electrodes located proximate to the selected electrode; and
  the surrogate cardiac electrical activation time generated from the electrical activity over the cardiac cycle monitored by the selected electrode is outside of a selected range from a median of the surrogate cardiac electrical activation times generated from the electrical activity monitored by the one or more electrodes located proximate to the selected electrode,
  wherein regenerating the surrogate cardiac electrical activation time based on the monitored electrical activity using correction criterion in response to a determination to correct the surrogate electrical activation time further comprises regenerating the surrogate cardiac electrical activation time based on the monitored electrical activity using the correlation correction criterion in response to determination to correct the surrogate cardiac electrical activation time with correlation correction.

48. The method of claim 47, wherein the correlation correction criterion defines a start time point and an end time point for the surrogate cardiac electrical activation time, wherein the end time point corresponds to a median end time point of the surrogate cardiac electrical activation times generated from the electrical activity monitored by the one or more electrodes located proximate to the selected electrode when regenerating the surrogate cardiac electrical activation time using correlation correction.

49. The method of claim 41, wherein the late correction criterion defines a start time point and an end time point for the surrogate cardiac electrical activation time, wherein the end time point is set to when the electrical activity is less than half of a maximum value of the electrical activity after occurrence of the maximum value of the electrical activity when regenerating the surrogate cardiac electrical activation time using late correction.

50. The method of claim 41, wherein the early correction criterion defines a start time point and an end time point for the surrogate cardiac electrical activation time, wherein the end time point is set to when the electrical activity is less than half of a minimum value of the electrical activity before occurrence of the minimum value of the electrical activity when regenerating the surrogate cardiac electrical activation time using early correction.

51. A system for use in cardiac evaluation comprising:
  electrode apparatus comprising a plurality of external electrodes to be located proximate a patient's skin; and
  computing apparatus comprising one or more processors, the computing apparatus coupled to the electrode apparatus and configured to:
    monitor electrical activity from the patient's skin using the plurality of external electrodes over a cardiac cycle,
    generate a surrogate cardiac electrical activation time based on the monitored electrical activity using baseline criterion,
    determine whether to correct the surrogate cardiac electrical activation time, wherein determining whether to correct the surrogate cardiac electrical activation time comprises determining to correct the surrogate cardiac electrical activation time with correlation correction if:
      a morphology of the electrical activity over the cardiac cycle monitored by a selected electrode is similar to the morphology of electrical activity over the cardiac cycle monitored by one or more electrodes located proximate to the selected electrode; and
      the surrogate cardiac electrical activation time generated from the electrical activity over the cardiac cycle monitored by the selected electrode is outside of a selected range from a median of the surrogate cardiac electrical activation times generated from the electrical activity monitored by the one or more electrodes located proximate to the selected electrode; and
    regenerate the surrogate cardiac electrical activation time based on the monitored electrical activity using correction criterion in response to a determination to correct the surrogate electrical activation time, wherein the correction criterion comprises at least one of early correction criterion, late correction criterion, and correlation criterion, wherein regenerating the surrogate cardiac electrical activation time based on the monitored electrical activity using correction criterion in response to a determination to correct the surrogate electrical activation time comprises regenerating the surrogate cardiac electrical activation time based on the monitored electrical activity using the correlation correction criterion in response to determination to correct the surrogate cardiac electrical activation time with correlation correction.

52. The system of claim 51, wherein monitoring electrical activity from the patient's skin using the plurality of external electrodes over a cardiac cycle comprises monitoring electrical activity from the patient's skin using the plurality of external electrodes over a cardiac depolarization cycle.

53. The system of claim 51, wherein the baseline criterion defines a start time point and an end time point for the surrogate cardiac electrical activation time, wherein the end time point corresponds to the time at which the maximum negative slope occurs within the electrical activity over the cardiac cycle.

54. The system of claim 51, wherein the correlation correction criterion defines a start time point and an end time point for the surrogate cardiac electrical activation time, wherein the end time point corresponds to a median end time point of the surrogate cardiac electrical activation times generated from the electrical activity monitored by the one or more electrodes located proximate to the selected electrode when regenerating the surrogate cardiac electrical activation time using correlation correction.

55. A method for use in cardiac evaluation comprising:
monitoring electrical activity from a patient's skin using a plurality of external electrodes to generate over a cardiac cycle;
generating a surrogate cardiac electrical activation time based on the monitored electrical activity using baseline criterion;
   determining whether to correct the surrogate cardiac electrical activation time wherein determining whether to correct the surrogate cardiac electrical activation time comprises determining to correct the surrogate cardiac electrical activation time with correlation correction if:
      a morphology of the electrical activity over the cardiac cycle monitored by a selected electrode is similar to the morphology of electrical activity over the cardiac cycle monitored by one or more electrodes located proximate to the selected electrode; and
      the surrogate cardiac electrical activation time generated from the electrical activity over the cardiac cycle monitored by the selected electrode is outside of a selected range from a median of the surrogate cardiac electrical activation times generated from the electrical activity monitored by the one or more electrodes located proximate to the selected electrode; and
regenerating the surrogate cardiac electrical activation time based on the monitored electrical activity using correction criterion in response to a determination to correct the surrogate electrical activation time, wherein the correction criterion comprises at least one of early correction criterion, late correction criterion, and correlation criterion, wherein regenerating the surrogate cardiac electrical activation time based on the monitored electrical activity using correction criterion in response to a determination to correct the surrogate electrical activation time comprises regenerating the surrogate cardiac electrical activation time based on the monitored electrical activity using the correlation correction criterion in response to determination to correct the surrogate cardiac electrical activation time with correlation correction.

56. The method of claim 55, wherein monitoring electrical activity from the patient's skin using the plurality of external electrodes over a cardiac cycle comprises monitoring electrical activity from the patient's skin using the plurality of external electrodes over a cardiac depolarization cycle.

57. The method of claim 55, wherein the baseline criterion defines a start time point and an end time point for the surrogate cardiac electrical activation time, wherein the end time point corresponds to the time at which the maximum negative slope occurs within the electrical activity over the cardiac cycle.

58. The method of claim 55, wherein the correlation correction criterion defines a start time point and an end time point for the surrogate cardiac electrical activation time, wherein the end time point corresponds to a median end time point of the surrogate cardiac electrical activation times generated from the electrical activity monitored by the one or more electrodes located proximate to the selected electrode when regenerating the surrogate cardiac electrical activation time using correlation correction.

* * * * *